United States Patent
Johnson et al.

(10) Patent No.: US 10,842,461 B2
(45) Date of Patent: Nov. 24, 2020

(54) SYSTEMS AND METHODS OF CHECKING REGISTRATIONS FOR SURGICAL SYSTEMS

(71) Applicant: GLOBUS MEDICAL, INC., Audubon, PA (US)

(72) Inventors: Norbert Johnson, North Andover, MA (US); Neil Crawford, Chandler, AZ (US); Jeffrey Forsyth, Cranston, RI (US)

(73) Assignee: Globus Medical, Inc., Audubon, PA (US)

( * ) Notice: Subject to any disclaimer, the term of this patent is extended or adjusted under 35 U.S.C. 154(b) by 747 days.

(21) Appl. No.: 15/347,841

(22) Filed: Nov. 10, 2016

(65) Prior Publication Data
US 2017/0119339 A1  May 4, 2017

Related U.S. Application Data

(63) Continuation-in-part of application No. 15/095,883, filed on Apr. 11, 2016, which is a continuation-in-part
(Continued)

(51) Int. Cl.
*A61B 6/00* (2006.01)
*A61B 90/96* (2016.01)
(Continued)

(52) U.S. Cl.
CPC .............. *A61B 6/58* (2013.01); *A61B 5/064* (2013.01); *A61B 6/461* (2013.01); *A61B 6/469* (2013.01);
(Continued)

(58) Field of Classification Search
CPC . A61B 6/00; A61B 17/17; A61B 2017/00477; A61B 2017/00876;
(Continued)

(56) References Cited

U.S. PATENT DOCUMENTS

| 4,150,293 A | 4/1979 | Franke |
| 5,020,933 A | 6/1991 | Salvestro et al. |

(Continued)

FOREIGN PATENT DOCUMENTS

| EP | 1103223 A2 | 5/2001 |
| EP | 1346687 A1 | 9/2003 |

(Continued)

OTHER PUBLICATIONS

Otake "Intraoperative Image-based Multiview 2D/3D Registration for Image-Guided Orthopaedic Surgery: Incorporation of Fiducial-Based C-Arm Tracking and GPU-Acceleration" IEEE Trans Med Imaging. Apr. 2012; 31(4): 948-962. (Year: 2012).*

(Continued)

*Primary Examiner* — Oommen Jacob

(57) ABSTRACT

A system and method of checking registration for a surgical system, the surgical system including fiducials and tracking markers, may include: using the fiducials and the tracking markers to register a three-dimensional (3D) imaging space of the surgical system with a 3D tracking space of the surgical system; using a tracking fixture of an X-ray imaging system to register an X-ray imaging space of the X-ray imaging system to the 3D tracking space; obtaining a two-dimensional (2D) X-ray image corresponding to the 3D tracking space; identifying a point of interest in the 2D X-ray image; determining a vector in the 3D tracking space that passes through the point of interest; and/or evaluating the registration of the 3D imaging space with the 3D tracking space based on a location, an orientation, or the location and the orientation of the vector in the 3D tracking space.

10 Claims, 28 Drawing Sheets

Related U.S. Application Data of application No. 14/062,707, filed on Oct. 24, 2013, now Pat. No. 10,357,184, which is a continuation-in-part of application No. 13/924,505, filed on Jun. 21, 2013, now Pat. No. 9,782,229.

(60) Provisional application No. 61/800,527, filed on Mar. 15, 2013, provisional application No. 61/662,702, filed on Jun. 21, 2012.

(51) Int. Cl.

| | |
|---|---|
| A61B 34/30 | (2016.01) |
| A61B 5/06 | (2006.01) |
| A61B 34/20 | (2016.01) |
| A61B 90/98 | (2016.01) |
| A61B 90/00 | (2016.01) |
| A61B 17/00 | (2006.01) |
| A61B 90/11 | (2016.01) |
| A61B 17/17 | (2006.01) |

(52) U.S. Cl.
CPC .............. *A61B 34/20* (2016.02); *A61B 34/30* (2016.02); *A61B 90/96* (2016.02); *A61B 90/98* (2016.02); *A61B 17/17* (2013.01); *A61B 90/11* (2016.02); *A61B 2017/00477* (2013.01); *A61B 2017/00876* (2013.01); *A61B 2034/2051* (2016.02); *A61B 2034/2055* (2016.02); *A61B 2034/2072* (2016.02); *A61B 2090/034* (2016.02); *A61B 2090/0811* (2016.02); *A61B 2090/363* (2016.02); *A61B 2090/376* (2016.02); *A61B 2090/3762* (2016.02); *A61B 2090/3937* (2016.02); *A61B 2090/3945* (2016.02); *A61B 2090/3966* (2016.02); *A61B 2560/0437* (2013.01)

(58) Field of Classification Search
CPC ...... A61B 2560/0437; A61B 2090/376; A61B 90/11; A61B 2090/034; A61B 2090/0811; A61B 2090/3762; A61B 2034/2051; A61B 2034/2055; A61B 2034/2072; A61B 2090/363; A61B 2090/3937; A61B 2090/3945; A61B 2090/3966; A61B 6/58; A61B 6/461; A61B 6/469; A61B 5/064; A61B 34/30; A61B 90/96; A61B 90/98; A61B 34/20
USPC .................................. 600/409, 407
See application file for complete search history.

(56) References Cited

U.S. PATENT DOCUMENTS

| | | | |
|---|---|---|---|
| 5,246,010 A | 9/1993 | Gazzara et al. | |
| 5,598,453 A | 1/1997 | Baba et al. | |
| 5,772,594 A | 6/1998 | Barrick | |
| 5,987,960 A | 11/1999 | Messner et al. | |
| 6,031,888 A | 2/2000 | Ivan et al. | |
| 6,144,875 A | 11/2000 | Schweikard et al. | |
| 6,203,196 B1 | 3/2001 | Meyer et al. | |
| 6,285,902 B1 * | 9/2001 | Kienzle, III | A61B 6/12 600/427 |
| 6,306,126 B1 | 10/2001 | Montezuma | |
| 6,314,311 B1 | 11/2001 | Williams et al. | |
| 6,320,929 B1 | 11/2001 | Von Der Haar | |
| 6,470,207 B1 * | 10/2002 | Simon | G06F 19/00 600/426 |
| 6,477,400 B1 | 11/2002 | Barrick | |
| 6,484,049 B1 | 11/2002 | Seeley et al. | |
| 6,487,267 B1 | 11/2002 | Wolter | |
| 6,490,475 B1 * | 12/2002 | Seeley | A61B 6/12 600/426 |
| 6,501,981 B1 | 12/2002 | Schweikard et al. | |
| 6,535,756 B1 | 3/2003 | Simon et al. | |
| 6,614,453 B1 | 9/2003 | Suri et al. | |
| 6,614,871 B1 | 9/2003 | Kobiki et al. | |
| 6,619,840 B2 | 9/2003 | Rasche et al. | |
| 6,666,579 B2 | 12/2003 | Jensen | |
| 6,711,433 B1 * | 3/2004 | Geiger | A61B 6/463 378/42 |
| 6,731,283 B1 * | 5/2004 | Navab | A61B 6/4441 345/424 |
| 6,757,068 B2 | 6/2004 | Foxlin | |
| 6,782,287 B2 * | 8/2004 | Grzeszczuk | A61B 90/36 600/424 |
| 6,856,826 B2 | 2/2005 | Seeley et al. | |
| 6,856,827 B2 * | 2/2005 | Seeley | A61B 6/12 250/362 |
| 6,892,090 B2 * | 5/2005 | Verard | A61B 34/20 600/424 |
| 6,920,347 B2 | 7/2005 | Simon et al. | |
| 6,922,632 B2 | 7/2005 | Foxlin | |
| 6,988,009 B2 | 1/2006 | Grimm et al. | |
| 6,996,487 B2 | 2/2006 | Jutras et al. | |
| 7,016,457 B1 | 3/2006 | Senzig et al. | |
| 7,043,961 B2 | 5/2006 | Pandey et al. | |
| 7,062,006 B1 | 6/2006 | Pelc et al. | |
| 7,063,705 B2 | 6/2006 | Young et al. | |
| 7,072,707 B2 | 7/2006 | Galloway, Jr. et al. | |
| 7,099,428 B2 | 8/2006 | Clinthorne et al. | |
| 7,108,421 B2 | 9/2006 | Gregerson et al. | |
| 7,130,676 B2 | 10/2006 | Barrick | |
| 7,139,418 B2 | 11/2006 | Abovitz et al. | |
| 7,194,120 B2 | 3/2007 | Wicker et al. | |
| 7,197,107 B2 | 3/2007 | Arai et al. | |
| 7,207,995 B1 | 4/2007 | Vandewalle | |
| 7,231,014 B2 | 6/2007 | Levy | |
| 7,231,063 B2 | 6/2007 | Naimark et al. | |
| 7,301,648 B2 | 11/2007 | Foxlin | |
| 7,313,430 B2 | 12/2007 | Urquhart et al. | |
| 7,318,805 B2 | 1/2008 | Schweikard et al. | |
| 7,324,623 B2 | 1/2008 | Heuscher et al. | |
| 7,327,865 B2 | 2/2008 | Fu et al. | |
| 7,460,637 B2 | 12/2008 | Clinthorne et al. | |
| 7,493,153 B2 | 2/2009 | Ahmed et al. | |
| 7,505,617 B2 | 3/2009 | Fu et al. | |
| 7,623,902 B2 | 11/2009 | Pacheco | |
| 7,643,862 B2 | 1/2010 | Schoenefeld | |
| 7,661,881 B2 | 2/2010 | Gregerson et al. | |
| 7,683,331 B2 | 3/2010 | Chang | |
| 7,683,332 B2 | 3/2010 | Chang | |
| 7,702,379 B2 | 4/2010 | Avinash et al. | |
| 7,702,477 B2 | 4/2010 | Tuemmler et al. | |
| 7,711,083 B2 | 5/2010 | Heigl et al. | |
| 7,725,253 B2 | 5/2010 | Foxlin | |
| 7,726,171 B2 | 6/2010 | Langlotz et al. | |
| 7,760,849 B2 | 7/2010 | Zhang | |
| 7,796,728 B2 | 9/2010 | Bergfjord | |
| 7,813,838 B2 | 10/2010 | Sommer | |
| 7,835,778 B2 | 11/2010 | Foley et al. | |
| 7,835,784 B2 | 11/2010 | Mire et al. | |
| 7,840,256 B2 | 11/2010 | Lakin et al. | |
| 7,844,320 B2 | 11/2010 | Shahidi | |
| 7,853,305 B2 | 12/2010 | Simon et al. | |
| 7,853,313 B2 | 12/2010 | Thompson | |
| 7,900,524 B2 | 3/2011 | Calloway et al. | |
| 7,940,999 B2 | 5/2011 | Liao et al. | |
| 7,945,012 B2 | 5/2011 | Ye et al. | |
| 7,945,021 B2 | 5/2011 | Shapiro et al. | |
| 8,019,045 B2 | 9/2011 | Kato | |
| 8,021,310 B2 | 9/2011 | Sanborn et al. | |
| 8,052,688 B2 | 11/2011 | Wolf, II | |
| 8,086,299 B2 | 12/2011 | Adler et al. | |
| 8,098,914 B2 | 1/2012 | Liao et al. | |
| 8,100,950 B2 | 1/2012 | St. Clair et al. | |
| 8,116,430 B1 | 2/2012 | Shapiro et al. | |
| 8,121,249 B2 | 2/2012 | Wang et al. | |
| 8,150,494 B2 | 4/2012 | Simon et al. | |
| 8,208,708 B2 | 6/2012 | Homan et al. | |
| 8,224,024 B2 | 7/2012 | Foxlin et al. | |
| 8,311,611 B2 | 11/2012 | Csavoy et al. | |

(56) References Cited

U.S. PATENT DOCUMENTS

| | | | |
|---|---|---|---|
| 8,313,430 B1 | 11/2012 | Pimenta | |
| 8,335,557 B2 | 12/2012 | Maschke | |
| 8,358,818 B2 | 1/2013 | Miga et al. | |
| 8,379,791 B2 | 2/2013 | Forthmann et al. | |
| 8,386,019 B2 | 2/2013 | Camus et al. | |
| 8,394,099 B2 | 3/2013 | Patwardhan | |
| 8,462,911 B2 | 6/2013 | Vesel et al. | |
| 8,526,700 B2 | 9/2013 | Isaacs | |
| 8,541,970 B2 | 9/2013 | Nowlin et al. | |
| 8,560,118 B2 | 10/2013 | Green et al. | |
| 8,597,198 B2 | 12/2013 | Sanborn et al. | |
| 8,611,983 B2 * | 12/2013 | Glossop | A61B 1/2676 600/414 |
| 8,611,985 B2 | 12/2013 | Lavallee et al. | |
| 8,630,389 B2 | 1/2014 | Kato | |
| 8,634,897 B2 | 1/2014 | Simon et al. | |
| 8,660,635 B2 | 2/2014 | Simon et al. | |
| 8,678,647 B2 | 3/2014 | Gregerson et al. | |
| 8,696,458 B2 | 4/2014 | Foxlin et al. | |
| 8,706,185 B2 | 4/2014 | Foley et al. | |
| 8,712,129 B2 * | 4/2014 | Strommer | G06K 9/32 382/128 |
| 8,727,618 B2 | 5/2014 | Maschke et al. | |
| 8,738,115 B2 | 5/2014 | Amberg et al. | |
| 8,740,882 B2 | 6/2014 | Jun et al. | |
| 8,781,186 B2 | 7/2014 | Clements et al. | |
| 8,781,630 B2 | 7/2014 | Banks et al. | |
| 8,787,520 B2 | 7/2014 | Baba | |
| 8,792,704 B2 | 7/2014 | Isaacs | |
| 8,798,231 B2 | 8/2014 | Notohara et al. | |
| 8,812,077 B2 | 8/2014 | Dempsey | |
| 8,814,793 B2 | 8/2014 | Brabrand | |
| 8,818,105 B2 | 8/2014 | Myronenko et al. | |
| 8,821,511 B2 | 9/2014 | Von Jako et al. | |
| 8,838,205 B2 * | 9/2014 | Shoham | A61B 17/1703 600/424 |
| 8,867,703 B2 | 10/2014 | Shapiro et al. | |
| 8,888,821 B2 | 11/2014 | Rezach et al. | |
| 8,964,934 B2 | 2/2015 | Ein-Gal | |
| 8,992,580 B2 | 3/2015 | Bar et al. | |
| 8,996,169 B2 | 3/2015 | Lightcap et al. | |
| 9,001,963 B2 | 4/2015 | Sowards-Emmerd et al. | |
| 9,002,076 B2 | 4/2015 | Khadem et al. | |
| 9,044,190 B2 | 6/2015 | Rubner et al. | |
| 9,107,683 B2 | 8/2015 | Hourtash et al. | |
| 9,119,670 B2 * | 9/2015 | Yang | A61B 5/055 |
| 9,125,556 B2 | 9/2015 | Zehavi et al. | |
| 9,131,986 B2 | 9/2015 | Greer et al. | |
| 9,215,968 B2 | 12/2015 | Schostek et al. | |
| 9,218,663 B2 * | 12/2015 | Lyon | A61B 90/39 |
| 9,308,050 B2 | 4/2016 | Kostrzewski et al. | |
| 9,380,984 B2 | 7/2016 | Li et al. | |
| 9,393,039 B2 | 7/2016 | Lechner et al. | |
| 9,398,886 B2 | 7/2016 | Gregerson et al. | |
| 9,398,890 B2 | 7/2016 | Dong et al. | |
| 9,414,859 B2 | 8/2016 | Ballard et al. | |
| 9,420,975 B2 | 8/2016 | Gutfleisch et al. | |
| 9,492,235 B2 | 11/2016 | Hourtash et al. | |
| 9,592,096 B2 | 3/2017 | Maillet et al. | |
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 11/2017 | Donner et al. | |
| 9,848,922 B2 | 12/2017 | Tohmeh et al. | |
| 9,925,011 B2 | 3/2018 | Gombert et al. | |
| 9,931,025 B1 | 4/2018 | Graetzel et al. | |
| 10,034,717 B2 | 7/2018 | Miller et al. | |
| 10,229,496 B2 * | 3/2019 | Strommer | G06K 9/32 |
| 10,255,721 B2 * | 4/2019 | Ruijters | G06T 19/20 |
| 10,492,741 B2 * | 12/2019 | Walker | A61B 6/032 |
| 2001/0036302 A1 | 11/2001 | Miller | |
| 2002/0077543 A1 * | 6/2002 | Grzeszczuk | A61B 34/20 600/424 |
| 2003/0073901 A1 * | 4/2003 | Simon | A61M 25/0105 600/424 |
| 2004/0034302 A1 | 2/2004 | Abovitz et al. | |
| 2004/0076259 A1 | 4/2004 | Jensen et al. | |
| 2004/0097806 A1 * | 5/2004 | Hunter | A61B 34/20 600/434 |
| 2005/0107679 A1 | 5/2005 | Geiger et al. | |
| 2005/0149045 A1 | 7/2005 | Elliott | |
| 2005/0171428 A1 * | 8/2005 | Fichtinger | A61N 5/1014 600/426 |
| 2005/0215888 A1 | 9/2005 | Grimm et al. | |
| 2006/0178559 A1 | 8/2006 | Kumar et al. | |
| 2006/0184396 A1 | 8/2006 | Dennis et al. | |
| 2006/0291612 A1 | 12/2006 | Nishide et al. | |
| 2007/0001879 A1 | 1/2007 | Kaftan et al. | |
| 2007/0038059 A1 | 2/2007 | Sheffer et al. | |
| 2007/0073133 A1 | 3/2007 | Schoenefeld | |
| 2007/0122020 A1 | 5/2007 | Claus et al. | |
| 2007/0238985 A1 | 10/2007 | Smith et al. | |
| 2008/0004523 A1 | 1/2008 | Jensen | |
| 2008/0013809 A1 | 1/2008 | Zhu et al. | |
| 2008/0082109 A1 | 4/2008 | Moll et al. | |
| 2008/0108991 A1 | 5/2008 | Von Jako | |
| 2008/0119725 A1 * | 5/2008 | Lloyd | A61B 34/20 600/424 |
| 2008/0119728 A1 * | 5/2008 | Frenkel | A61B 5/103 600/426 |
| 2008/0144906 A1 | 6/2008 | Allred et al. | |
| 2008/0154389 A1 | 6/2008 | Smith et al. | |
| 2008/0159612 A1 * | 7/2008 | Fu | G06T 11/008 382/131 |
| 2008/0161680 A1 | 7/2008 | Von Jako et al. | |
| 2008/0188934 A1 | 8/2008 | Moser et al. | |
| 2008/0200794 A1 | 8/2008 | Teichman et al. | |
| 2008/0235052 A1 | 9/2008 | Node-Langlois et al. | |
| 2008/0269596 A1 | 10/2008 | Revie et al. | |
| 2008/0287781 A1 | 11/2008 | Revie et al. | |
| 2008/0300477 A1 | 12/2008 | Lloyd et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0052757 A1 * | 2/2009 | Khamene | G06T 7/30 382/131 |
| 2009/0099445 A1 | 4/2009 | Burger | |
| 2009/0185655 A1 | 7/2009 | Koken et al. | |
| 2009/0198121 A1 | 8/2009 | Hoheisel | |
| 2009/0234217 A1 * | 9/2009 | Mire | A61B 34/20 600/407 |
| 2009/0306480 A1 | 12/2009 | Protopsaltis | |
| 2010/0022874 A1 | 1/2010 | Wang et al. | |
| 2010/0039506 A1 | 2/2010 | Sarvestani et al. | |
| 2010/0046718 A1 | 2/2010 | Weiser et al. | |
| 2010/0080354 A1 * | 4/2010 | Fu | G06T 5/50 378/65 |
| 2010/0125286 A1 | 5/2010 | Wang et al. | |
| 2010/0174410 A1 | 7/2010 | Greer et al. | |
| 2010/0228117 A1 | 9/2010 | Hartmann | |
| 2010/0274120 A1 | 10/2010 | Heuscher | |
| 2011/0040305 A1 | 2/2011 | Gomez et al. | |
| 2011/0098553 A1 | 4/2011 | Robbins et al. | |
| 2011/0184245 A1 | 7/2011 | Xia et al. | |
| 2011/0190588 A1 | 8/2011 | McKay | |
| 2011/0282189 A1 | 11/2011 | Graumann | |
| 2011/0286573 A1 | 11/2011 | Schretter et al. | |
| 2012/0035507 A1 | 2/2012 | George et al. | |
| 2012/0051498 A1 | 3/2012 | Koishi | |
| 2012/0143084 A1 | 6/2012 | Shoham | |
| 2012/0226145 A1 | 9/2012 | Chang et al. | |
| 2012/0235909 A1 | 9/2012 | Birkenbach et al. | |
| 2012/0289820 A1 | 11/2012 | Rohling | |
| 2012/0294498 A1 | 11/2012 | Popovic | |
| 2013/0016889 A1 | 1/2013 | Myronenko et al. | |
| 2013/0060146 A1 | 3/2013 | Yang et al. | |
| 2013/0094742 A1 | 4/2013 | Feilkas | |
| 2013/0113791 A1 | 5/2013 | Isaacs et al. | |
| 2013/0165937 A1 | 6/2013 | Patwardhan | |
| 2013/0165948 A1 | 6/2013 | Popovic | |
| 2013/0184873 A1 | 7/2013 | Namiki | |

(56) References Cited

U.S. PATENT DOCUMENTS

| | | |
|---|---|---|
| 2013/0279784 A1 | 10/2013 | Gill et al. |
| 2013/0281821 A1 | 10/2013 | Liu et al. |
| 2013/0307955 A1 | 11/2013 | Deitz et al. |
| 2013/0342578 A1 | 12/2013 | Isaacs |
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0052150 A1 | 2/2014 | Taylor et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135744 A1 | 5/2014 | Stein et al. |
| 2014/0145796 A1 | 5/2014 | Simon et al. |
| 2014/0200587 A1 | 7/2014 | Pompee et al. |
| 2014/0206990 A1* | 7/2014 | Epstein ............... A61B 6/12 600/425 |
| 2014/0130810 A1 | 8/2014 | Azizian et al. |
| 2014/0221819 A1 | 8/2014 | Sarment |
| 2014/0221822 A1 | 8/2014 | Ehlers et al. |
| 2014/0228631 A1 | 8/2014 | Kwak et al. |
| 2014/0234804 A1 | 8/2014 | Huang et al. |
| 2014/0275955 A1 | 9/2014 | Crawford et al. |
| 2014/0336669 A1 | 11/2014 | Park |
| 2014/0343416 A1 | 11/2014 | Panescu et al. |
| 2014/0357989 A1 | 12/2014 | Hendriks et al. |
| 2014/0371577 A1 | 12/2014 | Mallet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0157468 A1 | 6/2015 | Wakayama et al. |
| 2015/0196261 A1 | 7/2015 | Funk |
| 2015/0196365 A1 | 7/2015 | Kostrzewski et al. |
| 2015/0209056 A1 | 7/2015 | Shoham et al. |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0063707 A1 | 3/2016 | Masumoto |
| 2016/0166329 A1 | 6/2016 | Langan et al. |
| 2016/0235480 A1 | 8/2016 | Scholl et al. |
| 2016/0235493 A1 | 8/2016 | Leboeuf, II et al. |
| 2016/0249990 A1 | 9/2016 | Glozman et al. |
| 2016/0256225 A1 | 9/2016 | Crawford et al. |
| 2016/0296266 A1 | 10/2016 | Chandanson et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0079727 A1 | 3/2017 | Crawford et al. |
| 2017/0112552 A1 | 4/2017 | Sinnott et al. |
| 2017/0119339 A1* | 5/2017 | Johnson ............... A61B 90/98 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0258526 A1 | 9/2017 | Lang |
| 2017/0258535 A1 | 9/2017 | Crawford et al. |
| 2017/0265952 A1 | 9/2017 | Donhowe et al. |
| 2017/0273748 A1 | 9/2017 | Hourtash et al. |
| 2017/0296277 A1 | 10/2017 | Hourtash et al. |
| 2017/0312032 A1 | 11/2017 | Amanatullah et al. |
| 2017/0348061 A1 | 12/2017 | Joshi et al. |
| 2017/0360493 A1 | 12/2017 | Zucher et al. |
| 2018/0042464 A1 | 2/2018 | Arai et al. |
| 2018/0049825 A1 | 2/2018 | Kwon et al. |
| 2018/0064496 A1 | 3/2018 | Hladio et al. |
| 2018/0200016 A1 | 7/2018 | Chappuis |

FOREIGN PATENT DOCUMENTS

| | | |
|---|---|---|
| EP | 1523950 A1 | 4/2005 |
| EP | 2471483 A1 | 7/2012 |
| JP | 3-118053 A | 5/1991 |
| JP | 2007-044488 A | 2/2007 |
| JP | 2007-531543 A | 11/2007 |
| JP | 2008-538184 A | 10/2008 |
| JP | 2011-120782 A | 6/2011 |
| JP | 2013-541365 A | 11/2013 |
| JP | 2014036700 A | 2/2014 |
| JP | 2015-504721 A | 2/2015 |
| JP | 2015528713 A | 10/2015 |
| JP | 2016043211 A | 4/2016 |
| JP | 2016-193222 A | 11/2016 |
| JP | 2018011938 A | 1/2018 |
| JP | 2018-027288 A | 2/2018 |
| JP | 2018-114283 A | 7/2018 |
| WO | 03007198 A2 | 1/2003 |
| WO | 2005039417 A1 | 5/2005 |
| WO | 20090126953 A2 | 10/2009 |
| WO | 2012050634 A1 | 4/2012 |
| WO | 2013114823 A1 | 8/2013 |
| WO | 2013192598 A1 | 12/2013 |
| WO | 2014010760 A1 | 1/2014 |
| WO | 2015023665 A1 | 2/2015 |
| WO | 2015052718 A1 | 4/2015 |
| WO | 2015142762 A1 | 9/2015 |
| WO | 2016087539 A2 | 6/2016 |
| WO | 2016152255 A1 | 9/2016 |
| WO | 2016170372 A1 | 10/2016 |
| WO | 2017127202 A1 | 7/2017 |
| WO | 2017186799 A1 | 11/2017 |

OTHER PUBLICATIONS

Marintschev et al.: "Navigation of vertebro-pelvic fixations based on CT-fluoro macthing", European Spine Journal, Springer, Berlin, DE, vol. 19, No. 11, pp. 1921-1927, Jun. 16, 2010.

Markelj et al.: "A review of 3D/2D registration methods for image-guided interventions", Medical Image Analysis, Oxford University Press, Oxford, GB, vol. 16, No. 3,pp. 642-661, Apr. 1, 2012.

Gong Ren Hui etal.: "Interactive initialization of 2D/3D rigid registration", Medical Physics, AIP, Melville, NY, US, vol. 40, No. 12, 14 pages, Dec. 2013.

Dumenil A et al.: "A versatile intensity-based 3D/2D rigid registration compatible with mobile C-arm for endovascular treatment of abdominal aortic aneurysm", International Journal of Computer Assisted Radiology and Surgery, Springer, DE, vol. 11, No. 9, pp. 1713-1729, May 26, 2016.

* cited by examiner

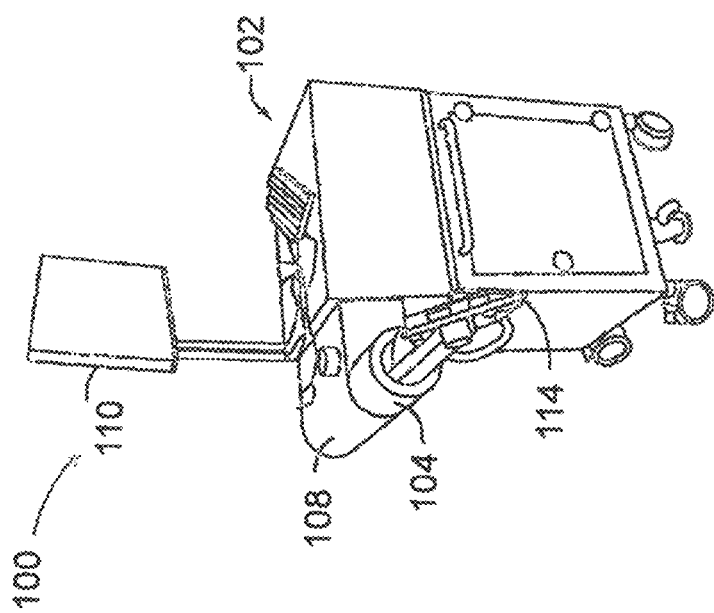

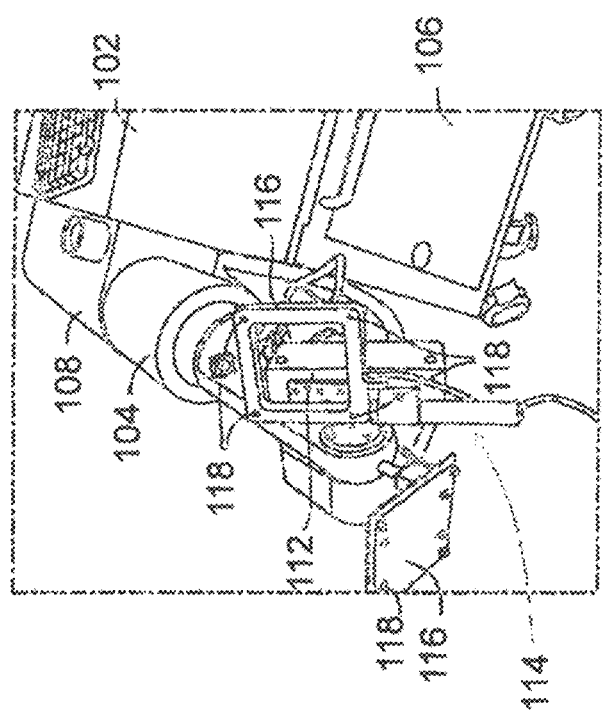

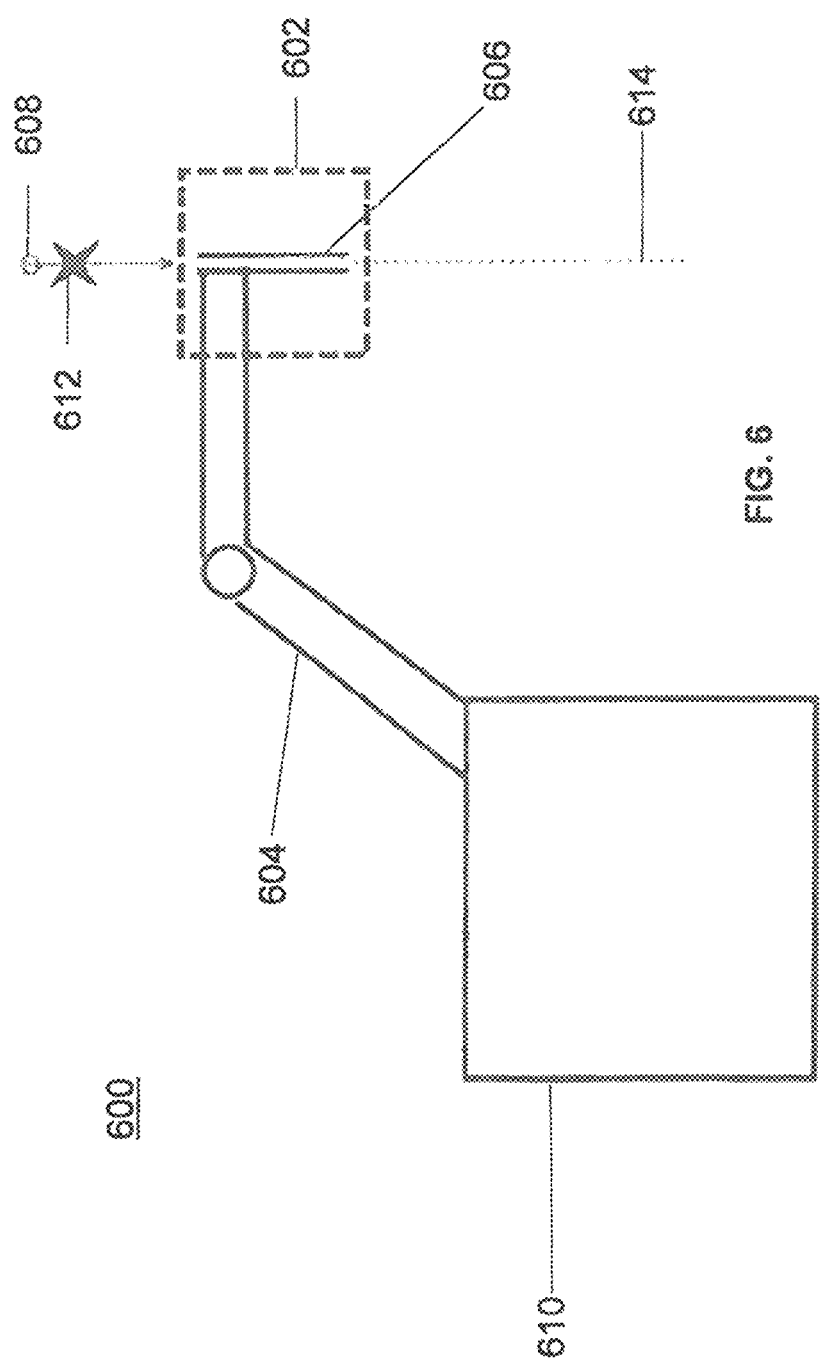

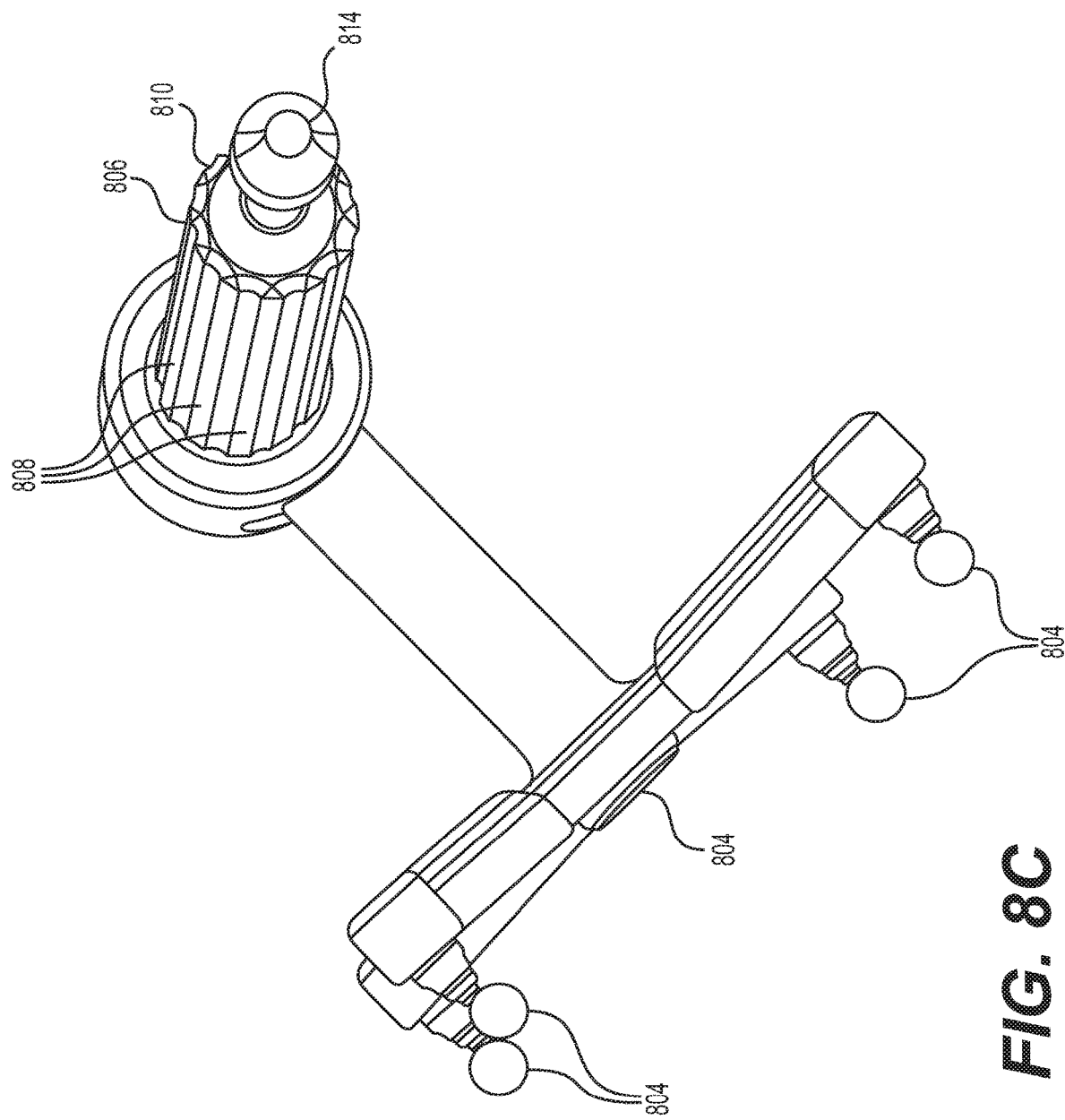

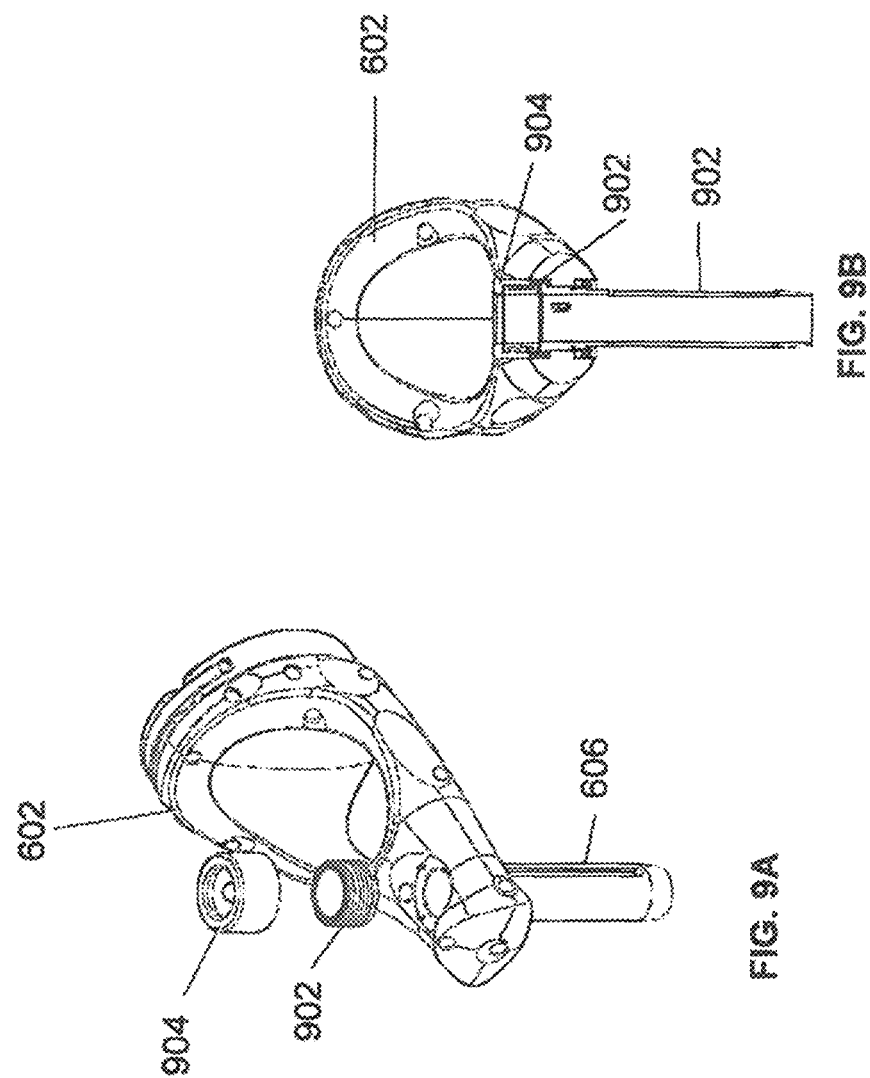

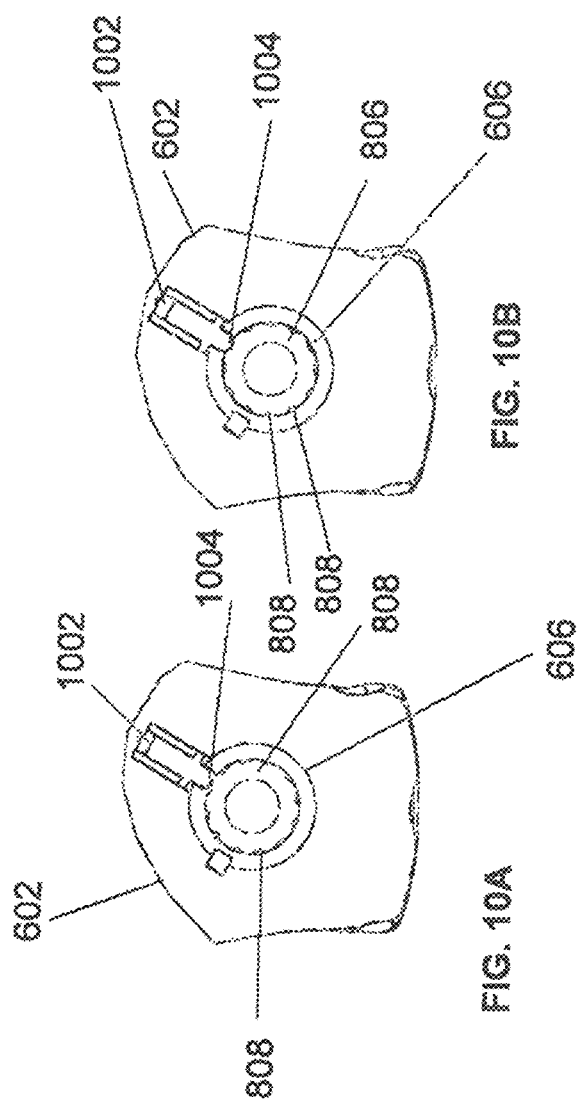

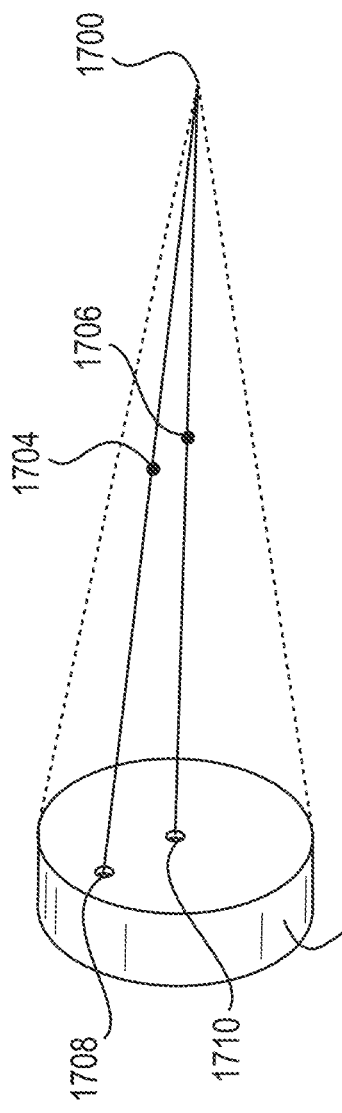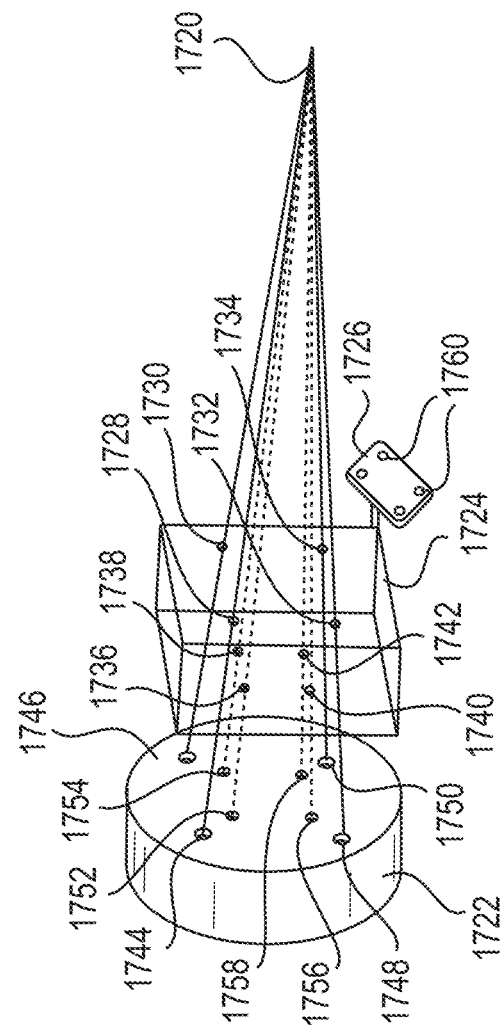

SYSTEMS AND METHODS OF CHECKING REGISTRATIONS FOR SURGICAL SYSTEMS

CROSS-REFERENCE TO RELATED APPLICATIONS

This application is a continuation-in-part of U.S. patent application Ser. No. 15/095,883 filed on Apr. 11, 2016 (published as U.S. Patent Publication No. 2016/0220320 A1). U.S. patent application Ser. No. 15/095,883 is a continuation-in-part application of U.S. patent application Ser. No. 14/062,707 filed on Oct. 24, 2013 (published as U.S. Patent Publication No. 2014/0275955 A1), which is a continuation-in-part application of U.S. patent application Ser. No. 13/924,505 filed on Jun. 21, 2013 (published as U.S. Patent Publication No. 2013/0345718 A1, with corrected publication as U.S. Patent Publication No. 2016/0242849 A9), which is a nonprovisional patent application that claims priority to U.S. provisional patent application No. 61/662,702 filed on Jun. 21, 2012, and claims priority to U.S. provisional patent application No. 61/800,527 filed on Mar. 15, 2013, the entire contents of all of which are incorporated herein by reference.

FIELD

The present disclosure generally relates to the use of robots in medical procedures and more particularly, the use of robots in surgical procedures that, for example, graphically depict anatomical structures of a patient on a display device and the location of surgical instruments in relation to those anatomical structures.

BACKGROUND

Various medical procedures require the accurate localization of a three-dimensional (3D) position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes including non-planar curved surfaces making accurate and perpendicular drilling difficult.

Conventionally, using currently-available systems and methods, a surgeon manually holds and positions a drill guide tube by using a guidance system to overlay the drill tube's position onto a three-dimensional image of the anatomical structures of a patient, for example, bone structures of the patient. This manual process is both tedious, time consuming, and error-prone. Further, whether the surgery can be considered successful largely depends upon the dexterity of the surgeon who performs it. Thus, there is a need for the use of robot assisted surgery to more accurately position surgical instruments and more accurately depict the position of those instruments in relation to the anatomical structures of the patient.

Currently, limited robotic assistance for surgical procedures is available. For example, certain systems allow a user to control a robotic actuator. These systems convert a surgeon's gross movements into micro-movements of the robotic actuator to more accurately position and steady the surgical instruments when undergoing surgery. Although these systems may aid in eliminating hand tremor and provide the surgeon with improved ability to work through a small opening, like many of the robots commercially available today, these systems are expensive, obtrusive, and require a cumbersome setup for the robot in relation to the patient and the user (e.g., a surgeon). Further, for certain procedures, such as thoracolumbar pedicle screw insertion, these conventional methods are known to be error-prone and tedious.

The current systems have many drawbacks including but not limited to the fact that autonomous movement and precise placement of a surgical instrument can be hindered by a lack of mechanical feedback and/or a loss of visual placement once the instrument is submerged within a portion of a patient. These drawbacks make the existing surgical applications error prone resulting in safety hazards to the patient as well as the surgeon during surgical procedures.

In addition, current robot assisted systems suffer from other disadvantages. The path and angle in which a surgical instrument is inserted into a patient (a trajectory of the instrument) may be limited due to the configuration of the robot arm and the manner in which it can move. For example, some current systems may not have enough range of motion or movement to place the surgical instrument at a trajectory ideal for placement into the patient and/or at a position that allows the surgeon an optimal view for performing the surgery.

The present disclosure overcomes the disadvantages of current robot assisted surgical applications. For example, the present disclosure allows for precisely locating anatomical structures in open, percutaneous, or minimally invasive surgery (MIS) procedures and positioning surgical instruments or implants during surgery. In addition, the present disclosure may improve stereotactic surgical procedures by allowing for identification and reference to a rigid anatomical structure relative to a pre-op computerized tomography (CT) scan, intra-operative CT scan, or fluoroscopy/X-ray based image of the anatomy. Further, the present disclosure may integrate a surgical robotic arm, a local positioning system, a dynamic reference base, and planning software to assist a surgeon in performing medical procedures in a more accurate and safe manner thereby reducing the error prone characteristics of current robot assisted systems and methods.

With respect to using image guidance for purposes robot-assisted surgery, coordinate systems relating to medical images may be registered with a navigation coordinate system. Registration is the quantification of the transformation between two or more coordinate systems. After successful registration, the position of a tool or other object in one coordinate system, such as an optically tracked space (navigation), can be accurately displayed in another coordinate system, such as the medical image space.

After registration, a check may be performed to determine if registration was successfully completed. One way of checking registration includes a qualitative and semi-quantitative anatomical check whereby a user touches a navigated tool (for example a tool having optical tracking markers) to a known point on the patient's anatomy and then verifies the accuracy of registration qualitatively by using computer software provided by the robotic system to determine whether the graphic representation of the tool is overlaid in the correct position relative to the anatomy on a computer monitor. As one example, the surgeon may touch a navigated probe to the tip of the surgically exposed spinous process. While pointing at this bony landmark, the graphic representation of the tool on the computer monitor should be displayed with its tip adjacent to the imaged spinous process on the medical image volume (CT or MRI).

The anatomical check is semi-quantitative because the user can see the offset of the graphic of the tool, if any, relative to the imaged bony process. Since the scale of the medical image is known, the user can roughly assess the distance by which the tool is offset from the bone, at least in the direction normal to the bone surface.

In the case of minimally invasive or endoscopic surgery, the anatomical check described above may have disadvantages because the surgeon is unable to position a navigated probe physically adjacent to bone since the bone is not exposed and does not directly contact the navigated tool. Therefore, an anatomical check of bony anatomy may not be performed by direct visual comparison, and would require touching the probe to the skin surface and estimating where the bony surface is relative to the skin surface. This estimation is a drawback since the surgeon may not be able to verify with a high degree of certainty whether the registration was accurate. Lack of verification may lead to errors in determining the locations and movements of the navigated tool on the computer monitor relative to the anatomy.

Therefore, a need exists for accurate methods of checking registration for surgical systems in, for example, minimally invasive, percutaneous, or endoscopic surgery.

SUMMARY

To meet this and other needs, devices, systems, and methods for using one or more intraoperative x-ray fluoroscopy images to perform a landmark check that does not require the surgeon to touch bone surfaces is provided. Additionally, such a check would allow more precise quantitative estimation of the error in registration, if any. Also provided is a manner for repairing registration if the registration is found to have sufficient and/or significant error In some example embodiments, a method of checking registration for a surgical system, the surgical system comprising fiducials and tracking markers, may comprise: using the fiducials and the tracking markers to register a three-dimensional (3D) imaging space of the surgical system with a 3D tracking space of the surgical system; using a tracking fixture of an X-ray imaging system to register an X-ray imaging space of the X-ray imaging system to the 3D tracking space; obtaining a two-dimensional (2D) X-ray image corresponding to the 3D tracking space; identifying a point of interest in the 2D X-ray image; determining a vector in the 3D tracking space that passes through the point of interest; and/or evaluating the registration of the 3D imaging space with the 3D tracking space based on a location, an orientation, or the location and the orientation of the vector in the 3D tracking space.

In some example embodiments, the surgical system may further comprise a processor. The vector in the 3D tracking space that passes through the point of interest may be determined by the processor.

In some example embodiments, the surgical system may further comprise a processor. The vector in the 3D tracking space that passes through the point of interest may be determined by the processor. The registration of the 3D imaging space with the 3D tracking space based on the location, the orientation, or the location and the orientation of the vector in the 3D tracking space may be evaluated by the processor.

In some example embodiments, the surgical system may further comprise a processor and a display. The vector in the 3D tracking space that passes through the point of interest may be determined by the processor and is shown on the display. The registration of the 3D imaging space with the 3D tracking space based on the location, the orientation, or the location and the orientation of the vector in the 3D tracking space may be evaluated by an operator of the surgical system using the display.

In some example embodiments, a method of checking registration for a surgical system, the surgical system comprising fiducials and tracking markers, may comprise: using the fiducials and the tracking markers to register a three-dimensional (3D) imaging space of the surgical system with a 3D tracking space of the surgical system; using a tracking fixture of an X-ray imaging system to register an X-ray imaging space of the X-ray imaging system to the 3D tracking space; obtaining a two-dimensional (2D) X-ray image of a patient corresponding to the 3D tracking space; identifying a point of interest of the patient; mapping the point of interest to the 2D X-ray image; determining a vector in the 3D tracking space that passes through the point of interest; and/or evaluating the registration of the 3D imaging space with the 3D tracking space based on a location of the point of interest in the 2D X-ray image; a location, an orientation, or the location and the orientation of the vector in the 3D tracking space; or the location of the point of interest in the 2D X-ray image and the location, the orientation, or the location and the orientation of the vector in the 3D tracking space.

In some example embodiments, the point of interest of the patient may be identified by an operator of the surgical system.

In some example embodiments, the surgical system may further comprise a processor.

The point of interest may be mapped to the 2D X-ray image by the processor.

In some example embodiments, the surgical system may further comprise a processor. The vector in the 3D tracking space that passes through the point of interest may be determined by the processor.

In some example embodiments, the surgical system may further comprise a processor. The vector in the 3D tracking space that passes through the point of interest may be determined by the processor. The registration of the 3D imaging space with the 3D tracking space based on the location, the orientation, or the location and the orientation of the vector in the 3D tracking space may be evaluated by the processor.

In some example embodiments, the surgical system may further comprise a processor and a display. The point of interest may be mapped to the 2D X-ray image by the processor and shown on the display. The vector in the 3D tracking space that passes through the point of interest may be determined by the processor and shown on the display. The registration of the 3D imaging space with the 3D tracking space based on the location of the point of interest in the 2D X-ray image; the location, the orientation, or the location and the orientation of the vector in the 3D tracking space; or the location of the point of interest in the 2D X-ray image and the location, the orientation, or the location and the orientation of the vector in the 3D tracking space may be evaluated by an operator of the surgical system using the display.

In some example embodiments, a method of checking registration for a surgical system, the surgical system comprising fiducials and tracking markers, may comprise: using the fiducials and the tracking markers to register a three-dimensional (3D) imaging space of the surgical system with a 3D tracking space of the surgical system; using a tracking fixture of an X-ray imaging system to register an X-ray imaging space of the X-ray imaging system to the 3D tracking space; obtaining a plurality of two-dimensional (2D) X-ray images corresponding to the 3D tracking space; identifying a point of interest in the 2D X-ray images; determining vectors in the 3D tracking space that pass through the point of interest; and/or evaluating the registration of the 3D imaging space with the 3D tracking space based on locations, orientations, or the locations and the orientations of the vectors in the 3D tracking space.

In some example embodiments, the surgical system may further comprise a processor. The vectors in the 3D tracking space that pass through the point of interest may be determined by the processor.

In some example embodiments, the surgical system may further comprise a processor. The vectors in the 3D tracking space that pass through the point of interest may be determined by the processor. The registration of the 3D imaging space with the 3D tracking space based on the locations, the orientations, or the locations and the orientations of the vectors in the 3D tracking space may be evaluated by the processor.

In some example embodiments, the surgical system may further comprise a processor and a display. The vectors in the 3D tracking spaces that pass through the point of interest may be determined by the processor and shown on the display. The registration of the 3D imaging space with the 3D tracking space based on the locations, the orientations, or the locations and the orientations of the vectors in the 3D tracking space may be evaluated by an operator of the surgical system using the display.

In some example embodiments, a method of checking registration for a surgical system, the surgical system comprising fiducials and tracking markers, may comprise: using the fiducials and the tracking markers to register a three-dimensional (3D) imaging space of the surgical system with a 3D tracking space of the surgical system; using a tracking fixture of an X-ray imaging system to register an X-ray imaging space of the X-ray imaging system to the 3D tracking space; obtaining a plurality of two-dimensional (2D) X-ray images corresponding to the 3D tracking space; identifying a point of interest in the 3D imaging space or the 3D tracking space; mapping the point of interest to the 2D X-ray images; and/or evaluating the registration of the 3D imaging space with the 3D tracking space based on a location of the point of interest in the 2D X-ray images.

In some example embodiments, the point of interest in the 3D imaging space or the 3D tracking space may be identified by an operator of the surgical system.

In some example embodiments, the surgical system may further comprise a processor. The point of interest in the 3D imaging space or the 3D tracking space may be identified by the processor.

In some example embodiments, the surgical system may further comprise a processor. The point of interest may be mapped to the 2D X-ray images by the processor.

In some example embodiments, the surgical system may further comprise a processor. The point of interest may be mapped to the 2D X-ray images by the processor. The registration of the 3D imaging space with the 3D tracking space based on the location of the point of interest in the 2D X-ray images may be evaluated by the processor.

In some example embodiments, the surgical system may further comprise a processor and a display. The point of interest may be mapped to the 2D X-ray images by the processor and is shown on the display. The registration of the 3D imaging space with the 3D tracking space based on the location of the point of interest in the 2D X-ray images may be evaluated by an operator of the surgical system using the display.

DESCRIPTION OF THE DRAWINGS

The above and/or other aspects and advantages will become more apparent and more readily appreciated from the following detailed description of example embodiments, taken in conjunction with the accompanying drawings, in which:

FIGS. 1A and 1B illustrate a surgical robot according to some example embodiments;

FIG. 1D illustrates a partial view of a surgical robot having a plurality of optical markers mounted for calibration and tracking movement according to some example embodiments;

FIG. 6 illustrates a surgical robot according to some example embodiments;

FIGS. 8A-8C illustrate an instrument and an instrument assembly according to some example embodiments;

FIGS. 9A and 9B illustrate an end-effector according to some example embodiments;

FIGS. 10A and 10B illustrate an end-effector and instrument assembly according to some example embodiments;

FIG. 15 illustrates a method of registration according to some example embodiments;

FIGS. 17A and 17B illustrate imaging systems according to some example embodiments;

DETAILED DESCRIPTION

Figure 1B:
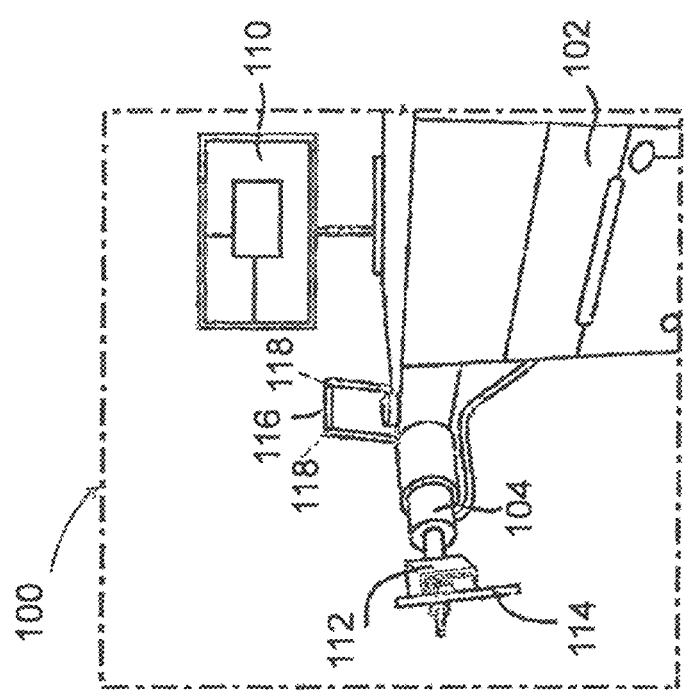

Example embodiments will now be described more fully with reference to the accompanying drawings. Embodiments, however, may be embodied in many different forms and should not be construed as being limited to the example embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIGS. 1A, 1B, and 1D illustrate a surgical robot system 100 according to some example embodiments. Surgical robot system 100 may include a surgical robot 102, a robot arm 104, a base 106, a housing 108, a display 110, an end-effector 112, a guide tube 114, a tracking array 116, and tracking markers 118.

Figure 1C:
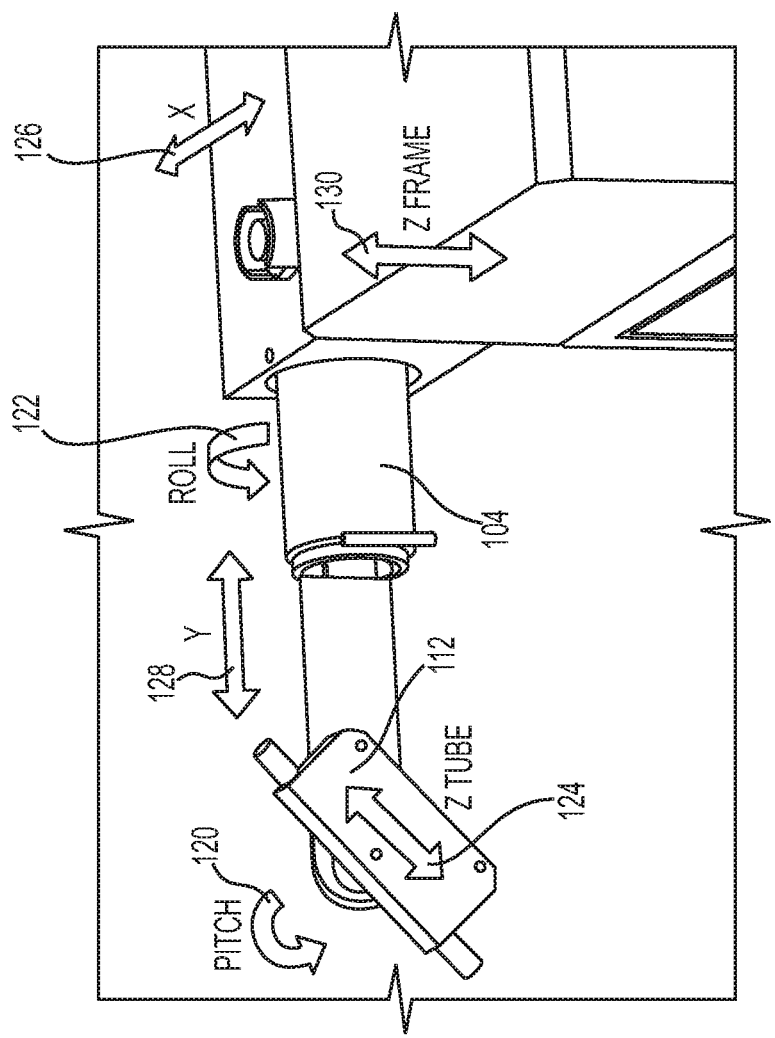
FIG. 1C illustrates a portion of a surgical robot with control of the translation and orientation of the end-effector according to some example embodiments.

FIG. 1C illustrates a portion of a surgical robot system 100 with control of the translation and orientation of end-effector 112 according to some example embodiments.

As shown in FIGS. 1A and 1B, surgical robot 102 can comprise a display 110 and a housing 108. Display 110 can be attached to the surgical robot 102 and in some example embodiments, display 110 can be detached from surgical robot 102, either within a surgical room with the surgical robot 102, or in a remote location. In some embodiments, housing 108 can comprise robot arm 104 and an end-effector 112. End-effector 112 may be coupled to the robot arm 104 and controlled by at least one motor. In some example embodiments, end-effector 112 can comprise a surgical instrument used to perform surgery on a patient 210. In some example embodiments, end-effector 112 can be coupled to the surgical instrument. As used herein, the term "end-effector" is used interchangeably with the term "effectuator element." In some embodiments, end-effector 112 can comprise any known structure for effecting the movement of the surgical instrument in a desired manner.

FIG. 1C illustrates a portion of a surgical robot 102 with control of the translation and orientation of end-effector 112 according to some example embodiments. As shown, some embodiments include a surgical robot system 100 capable of using surgical robot 102 with an ability to move end-effector 112 along x-, y-, and z-axes (see 126, 128, 130 in FIG. 1C). In this embodiment, x-axis 126 can be orthogonal to y-axis 128 and z-axis 130, y-axis 128 can be orthogonal to x-axis 126 and z-axis 130, and z-axis 130 can be orthogonal to x-axis 126 and y-axis 128. In some example embodiments, surgical robot 102 can be configured to effect movement of end-effector 112 along one axis independently of the other axes. For example, in some example embodiments, surgical robot 102 can cause the end-effector 112 to move a given distance of 500 millimeters (mm) or more along x-axis 126 without causing any substantial movement of end-effector 112 along y-axis 128 or z-axis 130. As used in this context "substantial" may mean a deviation of more than two degrees or 2 mm from an intended path or some other predetermined deviation that may be appropriate for the surgical application.

In some example embodiments, end-effector 112 can be configured for selective rotation about one or more of x-axis 126, y-axis 128, and a Z Frame axis 130 (such that one or more of the Euler Angles (e.g., roll, pitch, and/or yaw)

associated with end-effector 112 can be selectively controlled). For example, roll 122 is selective rotation about y-axis 128 without substantial deviation about or along x-axis 126 or Z Frame axis 130; pitch 120 is selective rotation about x-axis 126 without substantial deviation about or along y-axis 128 or Z Frame axis 130. In some example embodiments, during operation, end-effector 112 and/or the surgical instrument may be aligned with a selected orientation axis (labeled "Z Tube" 124 in FIG. 1C) that can be selectively varied and monitored by surgical robot system 100. End-effector 112 may contain a linear actuator that causes guide tube 114 to move in Z Tube axis 124 direction.

Figure 2:
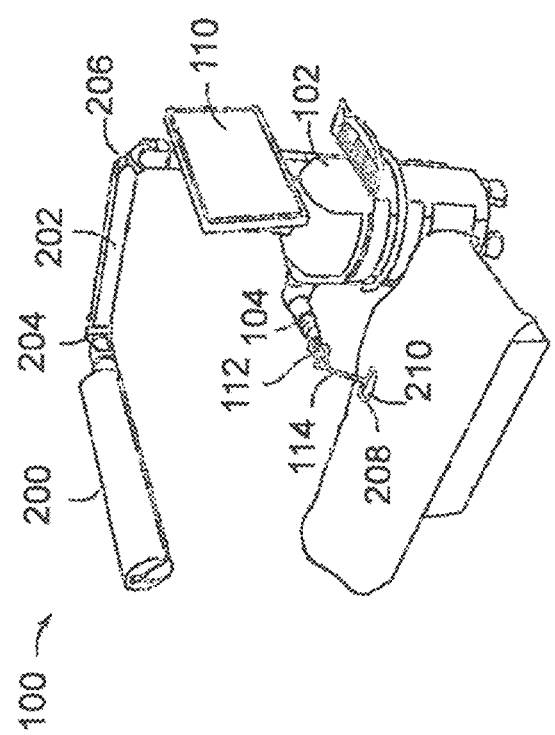
FIG. 2 illustrates a surgical robot operating on a patient according to some example embodiments.

In some example embodiments, selective control of the translation and orientation of end-effector 112 can permit performance of medical procedures with significantly improved accuracy compared to conventional robots that utilize, for example, a six degree of freedom robot arm comprising only rotational axes. For example, in some example embodiments, as shown in FIG. 2, surgical robot system 100 may be used to operate on patient 210, and robot arm 104 that can be positioned above the body of patient 210, with end-effector 112 selectively angled relative to the z-axis toward the body of patient 210.

In some example embodiments, the position of the surgical instrument can be dynamically updated so that surgical robot 102 can be aware of the location of the surgical instrument at all times during the procedure. Consequently, in some example embodiments, surgical robot 102 can move the surgical instrument to the desired position quickly, with minimal damage to patient 210, and without any further assistance from a physician (unless the physician so desires). In some further embodiments, surgical robot 102 can be configured to correct the path of the surgical instrument if the surgical instrument strays from the selected, preplanned trajectory. In some example embodiments, surgical robot 102 can be configured to permit stoppage, modification, and/or manual control of the movement of end-effector 112 and/or the surgical instrument. Thus, in use, in some example embodiments, a physician or other user can operate the surgical robot system 100, and has the option to stop, modify, or manually control the autonomous movement of end-effector 112 and/or the surgical instrument. Further details of surgical robot system 100 including the control and movement of a surgical instrument by surgical robot 102 can be found in co-pending U.S. patent application Ser. No. 13/924,505 from which this application claims priority under 35 U.S.C. § 120, and which is incorporated herein by reference in its entirety.

As shown in FIGS. 1B and 1D, in some example embodiments, surgical robot system 100 can comprise a plurality of tracking markers 118 configured to track the movement of robot arm 104, end-effector 112, and/or the surgical instrument in three dimensions. It should be appreciated that three-dimensional positional information from tracking markers 118 can be used in conjunction with the one dimensional linear or rotational positional information from absolute or relative conventional linear or rotational encoders on each axis of surgical robot 102 to maintain a high degree of accuracy. In some example embodiments, the plurality of tracking markers 118 can be mounted (or otherwise secured) thereon an outer surface of the surgical robot 102, such as, for example and without limitation, on base 106 of surgical robot 102, or robot arm 104 (see for example FIG. 1B). Further, in some example embodiments, the plurality of tracking markers 118 can be positioned on base 106 of surgical robot 102 spaced from surgical field 208 to reduce the likelihood of being obscured by the surgeon, surgical tools, or other parts of surgical robot 102. In some example embodiments, at least one tracking marker 118 of the plurality of tracking markers 118 can be mounted or otherwise secured to end-effector 112 (see for example FIG. 1D).

In some example embodiments, surgical robot system 100 can use tracking information collected relative to base 106 to calculate the orientation and coordinates of the surgical instrument held in guide tube 114 based on encoder counts along x-axis 126, y-axis 128, z-axis 130, Z-tube axis 124, and the roll 122 and pitch 120 axes.

In some example embodiments, one or more of tracking markers 118 may be optical markers and at least one optical marker may be positioned on the surgical robot 102 between base 106 of surgical robot 102 and end-effector 112 instead of, or in addition to, other tracking markers 118 on base 106. In some embodiments, the positioning of one or more tracking markers 118 on end-effector 112 can maximize the accuracy of the positional measurements by serving to check or verify the position of end-effector 112 (calculated from the positional information of tracking markers 118 on base 106 and encoder counts of z-axis 130, x-axis 126, y-axis 128, roll axis 122, pitch axis 120, and Z-tube axis 124).

In some example embodiments, the at least one tracking marker 118 can be mounted to a portion of the surgical robot 102 that effects movement of end-effector 112 and/or the surgical instrument along the x-axis to enable the at least one tracking marker 118 to move along x-axis 126 as end-effector 112 and the surgical instrument move along the x-axis 126 (see FIG. 1D). In some example embodiments, placement of tracking markers 118 as described can reduce the likelihood of a surgeon blocking one or more tracking markers 118 from the cameras or detection device, or one or more tracking markers 118 becoming an obstruction to surgery.

In some example embodiments, because of the high accuracy in calculating the orientation and position of end-effector 112 based on an output of one or more of tracking markers 118 and/or encoder counts from each axis, it can be possible to very accurately determine the position of end-effector 112. For example, in some example embodiments, without requiring knowledge of the counts of axis encoders for the z-axis 130 (which is between the x-axis 126 and base 106), knowing only the position of tracking markers 118 on the x-axis 126 and the counts of encoders on the y-axis 128, roll axis 122, pitch axis 120, and Z-tube axis 124 can enable computation of the position of end-effector 112. In some embodiments, the placement of tracking markers 118 on any intermediate axis of surgical robot 102 can permit the exact position of end-effector 112 to be calculated based on location of such tracking markers 118 and counts of encoders on axes (126, 120, 122, and 124) between tracking markers 118 and end-effector 112. Further details of surgical robot system 100 including the control, movement and tracking of surgical robot 102 and of a surgical instrument can be found in co-pending U.S. patent application Ser. No. 13/924,505 from which this application claims priority under 35 U.S.C. § 120, and which is incorporated herein by reference in its entirety as earlier recited.

In some example embodiments, one or more markers may be coupled to the surgical instrument as described in greater detail below. In some example embodiments, these markers as well as tracking markers 118 can comprise conventional infrared light-emitting diodes or an Optotrak® diode capable of being tracked using a commercially available infrared optical tracking system such as Optotrak®. Optotrak® is a registered trademark of Northern Digital Inc., Waterloo, Ontario, Canada. In some example embodiments, tracking markers 118 can comprise conventional reflective spheres capable of being tracked using a commercially available optical tracking system such as Polaris Spectra®. Polaris Spectra® is also a registered trademark of Northern Digital, Inc.

Referring to FIG. 2, surgical robot system 100 is shown and further includes camera 200, a camera arm 202, and camera arm joints 204 and 206. FIG. 2 further depicts surgical field 208 and patient 210.

In some example embodiments, light emitted from and/or reflected by tracking markers 118 and markers on the surgical instrument can be read by camera 200 and can be used to monitor the location and movement of surgical robot 102 (see for example camera 200 mounted on the camera arm 202 and capable of movement through camera arm joint 204 and camera arm joint 206 shown in FIG. 2). In some example embodiments, tracking markers 118 and the markers on the surgical instrument can comprise a radio-frequency and/or electromagnetic reflector or transceiver and the camera 200 can include or be replaced by a radio-frequency and/or electromagnetic transceiver.

Figure 3:
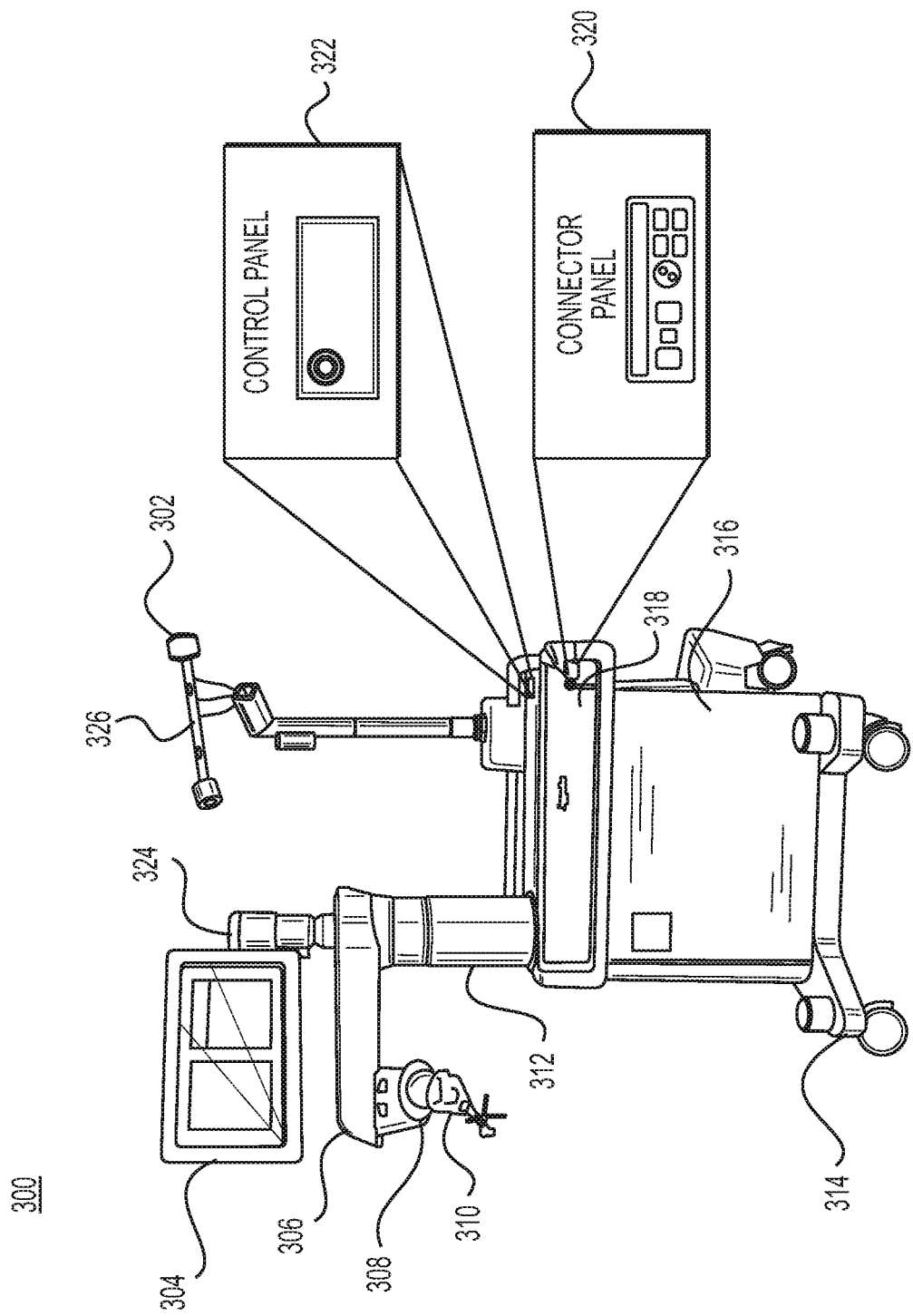
FIG. 3 illustrates a surgical robot according to some example embodiments.

FIG. 3 illustrates surgical robot system 300 and camera stand 302 consistent with some example embodiments. Surgical robot system 300 may comprise display 304, upper arm 306, lower arm 308, end-effector 310, vertical column 312, casters 314, cabinet 316, tablet drawer 318, connector panel 320, control panel 322, and ring 324. Camera stand 302 may comprise camera 326. These components are described in greater with respect to FIG. 5.

Figure 4:
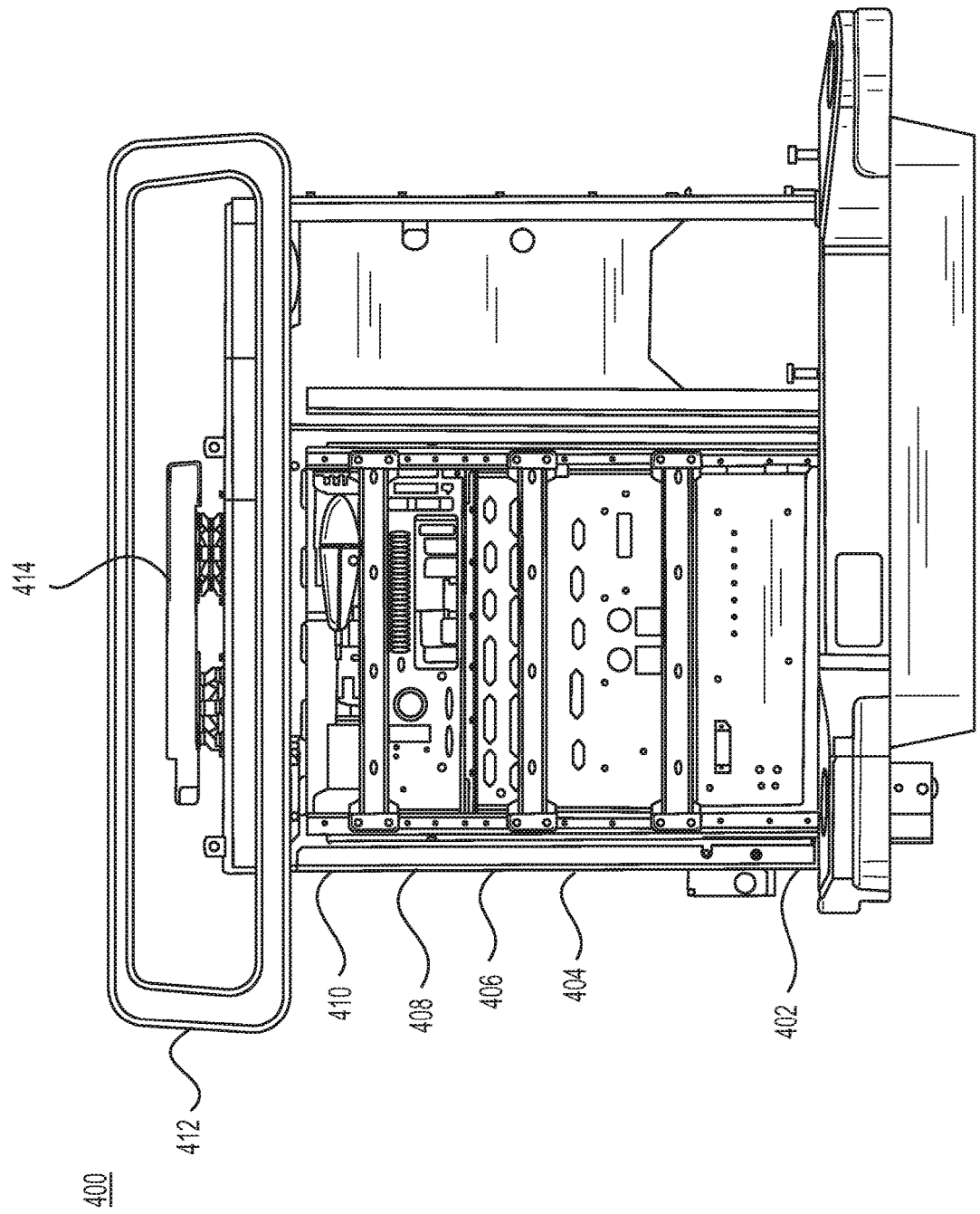
FIG. 4 illustrates a portion of a surgical robot according to some example embodiments.

FIG. 4 illustrates a base 400 consistent with some example embodiments. Base 400 may be a portion of surgical robot system 300 and comprise cabinet 316. Cabinet 316 may house certain components of surgical robot system 300 including but not limited to battery 402, power distribution module 404, platform interface board module 406, computer 408, additional components 410, handle 412, and tablet drawer 414. The connections and relationship between these components is described in greater detail with respect to FIG. 5.

Figure 5:
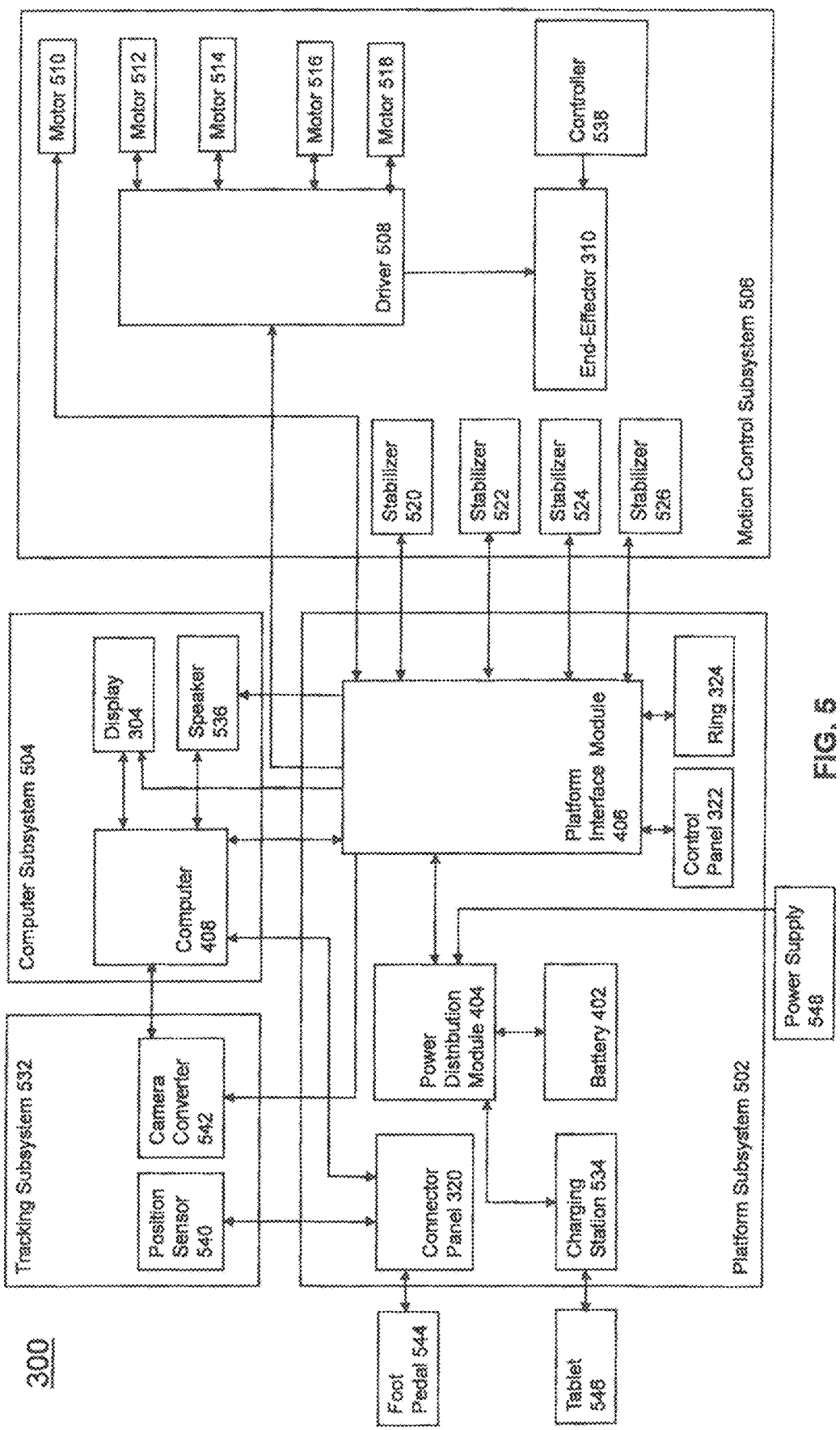
FIG. 5 illustrates a block diagram of a surgical robot according to some example embodiments.

FIG. 5 illustrates a block diagram of certain components of some example embodiments of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. surgical robot system 300 may also comprise a foot pedal 544 and tablet 546.

Input power is suppled to surgical robot system 300 via power supply 548 which may be provided to power distribution module 404. Power distribution module 404 receives input power and is configured to generate different power supply voltages that are provided to other modules, components, and subsystems of surgical robot system 300. Power distribution module 404 may be configured to provide different voltage supplies to platform interface board module 406, which may be provided to other components such as computer 408, display 304, speaker 536, driver circuit 508 to, for example, power motors 512, 514, 516, 518 and end-effector 310, motor 510, ring 324, camera converter 542, and other components for surgical robot system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging tablet 546. Tablet 546 may be used by a surgeon consistent with the present disclosure and described herein.

Power distribution module 404 may also be connected to battery 402, which serves as temporary power source in the event that power distribution module 404 does not receive power from power supply 548. At other times, power distribution module 404 may serve to charge battery 402 if necessary.

Other components of platform subsystem 502 may also include connector panel 320, control panel 322, and ring 324. Connector panel 320 may serve to connect different devices and components to surgical robot system 300 and/or associated components and modules. Connector panel 320 may contain one or more ports that receive lines or connections from different components. For example, connector panel 320 may have a ground terminal port that may ground surgical robot system 300 to other equipment, a port to connect foot pedal 544 to surgical robot system 300, a port to connect to tracking subsystem 532, which may comprise position sensor 540, camera converter 542, and camera 326 associated with camera stand 302. Connector panel 320 may also include other ports to allow Universal Serial Bus (USB), Ethernet, High-Definition Multimedia Interface (HDMI) communications to other components, such as computer 408.

Control panel 322 may provide various buttons or indicators that control operation of surgical robot system 300 and/or provide information regarding surgical robot system 300. For example, control panel 322 may include buttons to power on or off surgical robot system 300, lift or lower vertical column 312, and lift or lower stabilizers 520, 522, 524, 526 that may be designed to engage casters 314 to lock surgical robot system 300 from physically moving. Other buttons may stop surgical robot system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of surgical robot system 300 of different modes that surgical robot system 300 is operating under and certain warnings to the user.

Computer subsystem 504 includes computer 408, display 304, and speaker 536. Computer subsystem 504 includes an operating system and software to operate surgical robot system 300. Computer subsystem 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 540 and camera converter 542. Tracking subsystem 532 may correspond to camera stand 302 including camera 326 as described with respect to FIG. 3. Position sensor 540 may be camera 326. Tracking subsystem may track the location of certain markers that are located on the different components of surgical robot system 300 and/or instruments used by a user during a surgical procedure. This tracking may be conducted in a manner consistent with the present disclosure including the use of infrared technology that tracks the location of active or passive elements, such as light-emitting diodes (LEDs) or reflective markers, respectively. The location, orientation, and position of structures having these types of markers may be provided to computer 408 which may be shown to a user on display 304. For example, a surgical instrument having these types of markers and tracked in this manner (which may be referred to as a navigational space) may be shown to a user in relation to a three-dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510, 512, 514, 516, 518. For example, motor 510 may be configured to vertically lift or lower vertical column 312. Motor 512 may be configured to laterally move upper arm 306 around a point of engagement with vertical column 312 as shown in FIG. 3. Motor 514 may be configured to laterally move lower arm 308 around a point of engagement with upper arm 306 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move surgical robot system 300 in a desired manner.

Moreover, surgical robot system 300 may provide for automatic movement of vertical column 312, upper arm 306, and lower arm 308 through a user indicating on display 304 (which may be a touchscreen input device) the location of a surgical instrument or component on a three-dimensional image of the patient's anatomy on display 304. The user may initiate this automatic movement by stepping on foot pedal 544 or some other input means.

FIG. 6 illustrates a surgical robot system 600 consistent with some example embodiments. Surgical robot system 600 may comprise end-effector 602, robot arm 604, guide tube 606, instrument 608, and robot base 610. Instrument 608 may be attached to a tracking array 612 and have an associated trajectory 614. Trajectory 614 may represent a path of movement that instrument 608 is configured to travel once it is secured in guide tube 606, for example, a path of insertion of instrument 608 into a patient. In some example embodiments, robot base 610 may be configured to be in electronic communication with robot arm 604 and end-effector 602 so that surgical robot system 600 may assist a user (for example, a surgeon) in operating on a patient. Surgical robot system 600 may be consistent with previously described surgical robot system 100 and/or surgical robot system 300.

A tracking array 612 may be mounted on instrument 608 to monitor the location and orientation of instrument 608. As described in greater detail below with respect to FIG. 8A, tracking array 612 may be attached to an instrument assembly 802 and may comprise markers 804. Instrument assembly 802 may house instrument 608 as described in further detail below with respect to FIG. 8B. Markers 804 may be, for example, light-emitting diodes and/or other types of markers as described consistent with the present disclosure. The tracking devices may be one or more line of sight devices associated with the surgical robot system. As an example, the tracking devices may be cameras associated with the surgical robot system and may also track tracking array 612 for a defined domain or relative orientations of the instrument in relation to the robot arm, the robot base, and/or a patient. The tracking devices may be consistent with those structures described in connection with camera stand 302 and tracking subsystem 532.

Figure 7A:
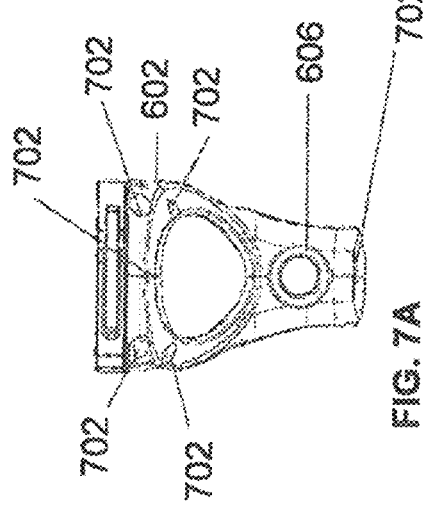
FIGS. 7A-7C illustrate an end-effector according to some example embodiments.
Figure 7B:
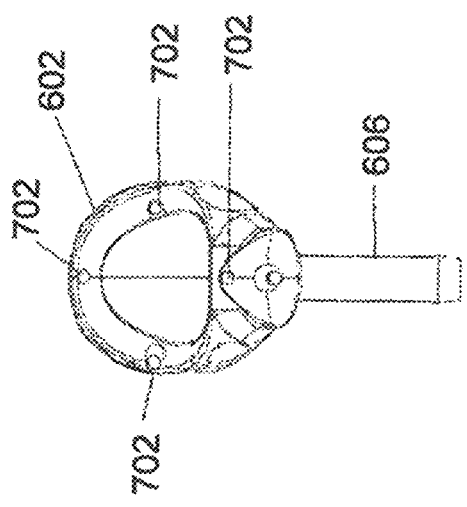
Figure 7C:
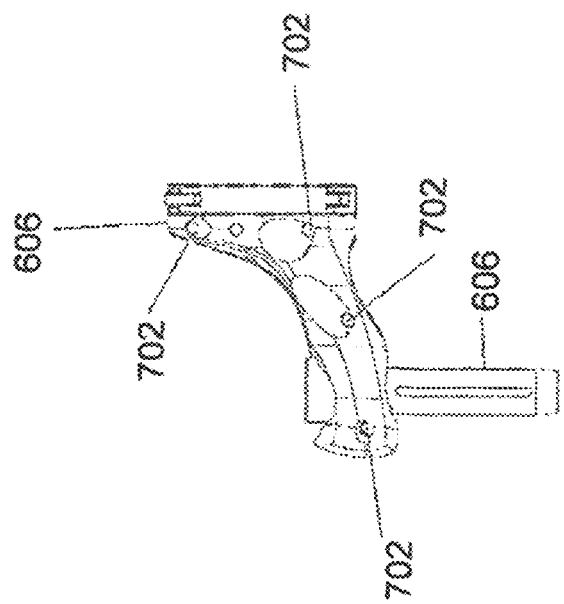

FIGS. 7A-7C illustrate a top view, front view, and side view, respectively, of end-effector 602 consistent with some example embodiments. End-effector 602 may additionally comprise one or more markers 702. Markers 702 may be light-emitting diodes or other types of markers that have been previously described.

Markers 702 may be disposed on end-effector 602 in a manner such that the markers are visible by one or more tracking devices associated with the surgical robot system. The tracking devices may track end-effector 602 as it moves to different positions and viewing angles by following the movement of tracking markers 702. The location of markers 702 and/or end-effector 602 may be shown on a display associated with the surgical robot system, for example, display 110 as shown in FIG. 1 and/or display 304 shown in FIG. 3. This display may allow a user to ensure that end-effector 602 is in a desirable position in relation to robot arm 604, robot base 610, the patient, and/or the user.

For example, as shown in FIG. 7A, markers 702 may be placed around the surface of end-effector 602 so that a tracking device placed away from the surgical field and facing toward the robot and surgical field is able to view at least 3 of the markers 702 through a range of common orientations of the end-effector relative to the tracking device. For example, distribution of markers in this way allows end-effector 602 to be monitored by the tracking devices when end-effector 602 is rotated by +/−135 degrees about the z-axis of the surgical robot system.

In addition, in some example embodiments, end-effector 602 may be equipped with infrared (IR) receivers that can detect when an external camera is getting ready to read markers 702. Upon this detection, end-effector 602 may then illuminate markers 702. The detection by the IR receivers that the external camera is ready to read markers 702 may signal the need to synchronize a duty cycle of markers 702, which may be light-emitting diodes, to an external camera. This may also allow for lower power consumption by the robotic system as a whole, whereby markers 702 would only be illuminated at the appropriate time instead of being illuminated continuously. Further, in some example embodiments, markers 702 may be powered off to prevent interference with other navigation tools, such as different types of surgical instruments.

Figure 8A:
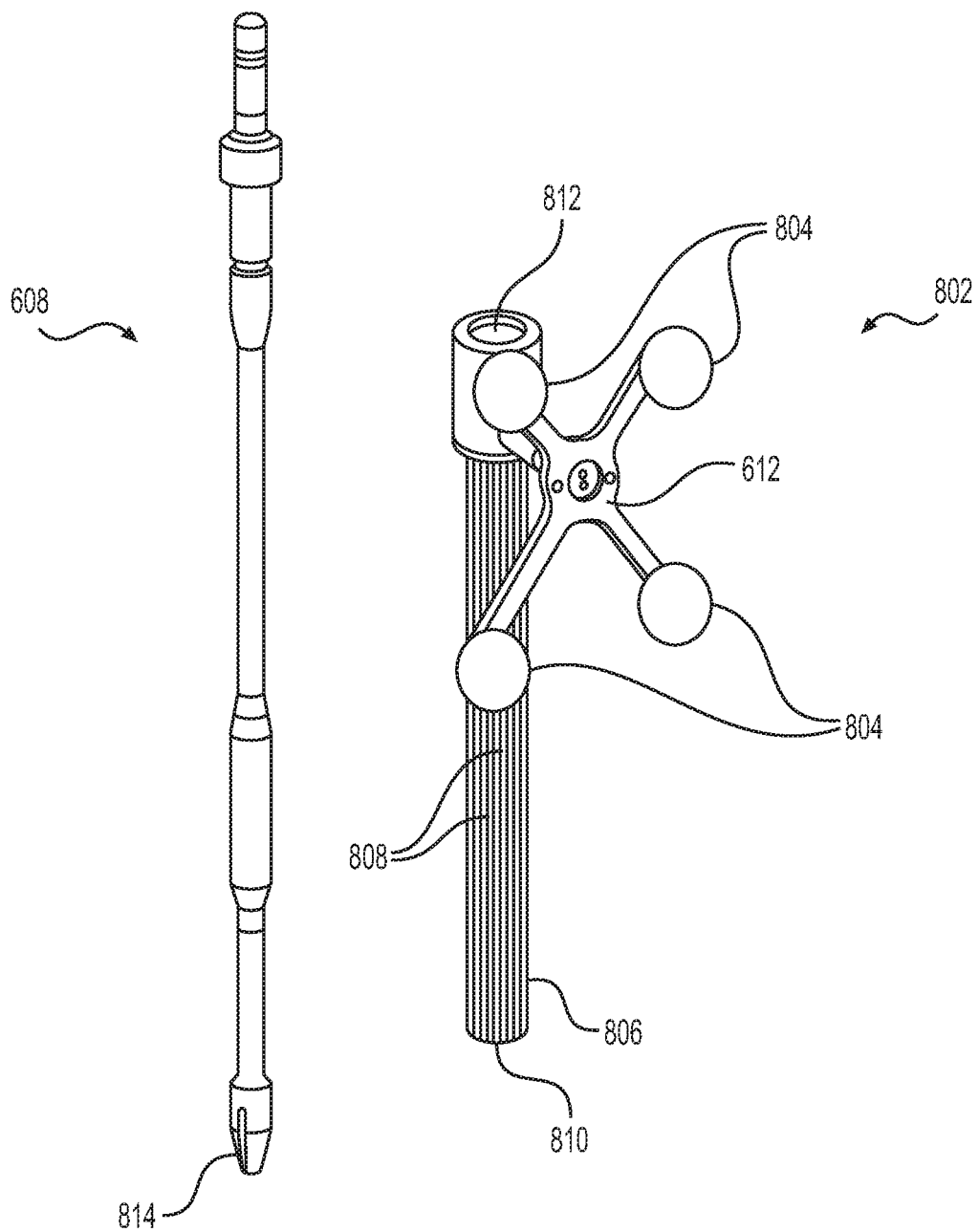

FIG. 8A depicts instrument 608 and instrument assembly 802. Instrument assembly 802 may further comprise tracking array 612, markers 804, an outer sleeve 806, one or more grooves 808, a tip 810, and an opening 812. Instrument 608 may include tip 814. Ultimately, as explained in greater detail with respect to FIGS. 10A and 10B, instrument assembly 802, which may house instrument 608, may be inserted into guide tube 606.

Markers 804 may be of any type described herein including but not limited to light-emitting diodes or reflective spheres. Markers 804 are monitored by tracking devices associated with the surgical robot system and may be one or more line of sight cameras. The cameras may track the location of instrument assembly 802 based on the position and orientation of tracking array 612 and markers 804. A user, such as a surgeon, may orient instrument assembly 802 in a manner so that tracking array 612 and markers 804 are sufficiently recognized by the tracking devices to display instrument assembly 802 and markers 804 on, for example, display 110 of surgical robot system 600. The manner in which a surgeon may place instrument assembly 802 into guide tube 606 and adjust instrument assembly 802 is explained in greater detail below.

Instrument assembly 802 may also include outer sleeve 806. Outer sleeve 806 may contain one or more grooves 808 and tip 810. As explained in greater detail below, tip 810 may contain lead-in features that assist in lining up one of grooves 808 with certain features of guide tube 606 to orient instrument assembly 802. The manner in which a user inserts instrument assembly 802 into guide tube 606 is explained in further detail with respect to FIGS. 10A and 10B.

Figure 8B:
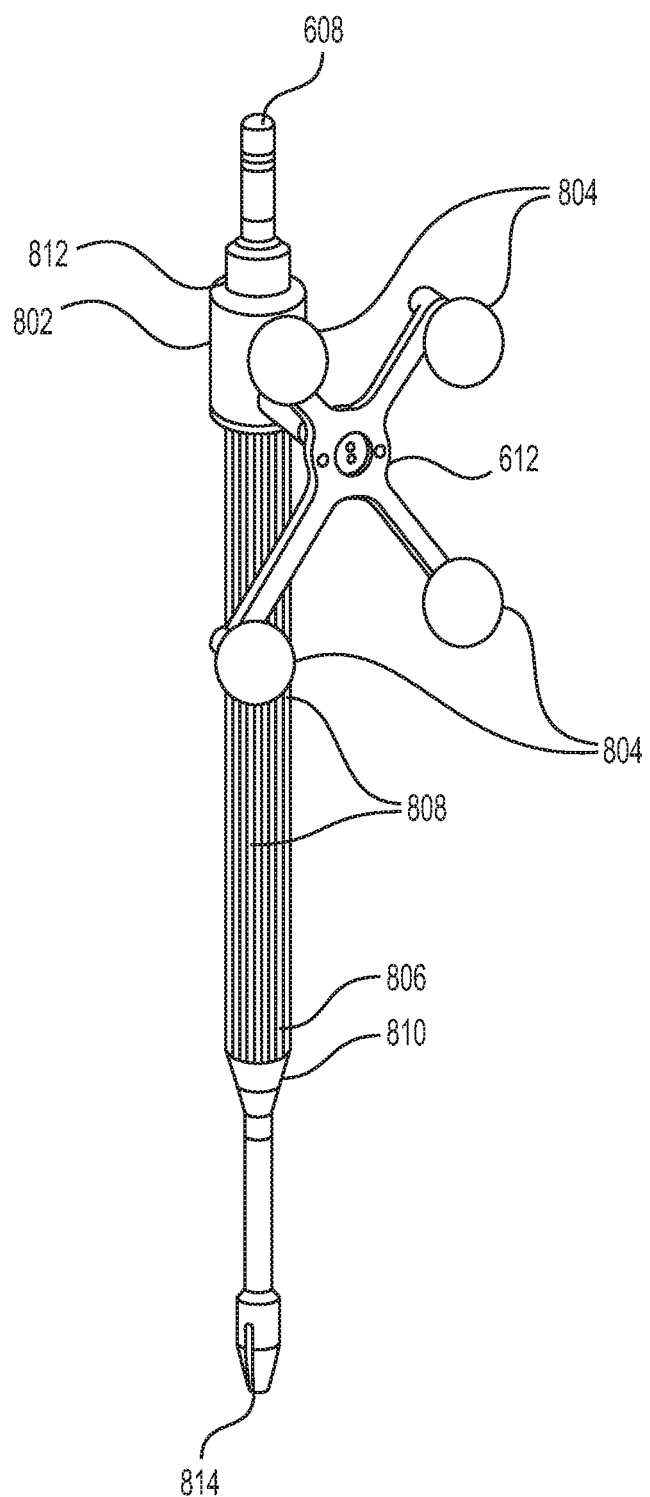

FIG. 8A also depicts instrument 608. Instrument 608 may be a surgical tool or implement associated with the surgical robot system. Instrument 608 may be inserted into instrument assembly 802 by inserting tip 814 into opening 812. Once inside instrument assembly 802, instrument 608 is free to rotate about its shaft axis and move in an axial direction as determined by the user. FIG. 8B depicts instrument 608 inserted into instrument assembly 802. FIG. 8C depicts a bottom view of instrument 608 inserted into instrument assembly 802.

FIGS. 9A and 9B illustrate end-effector 602 consistent with some example embodiments. End-effector 602 may comprise sensor 902 and sensor cover 904. The surgical robot system may contain circuitry that is configured to restrict or prevent robot arm 604 from moving when an instrument (for example, instrument 608) is in guide tube 606. Restricting or preventing movement of robot arm 604 while instrument 608 or another surgical instrument is in guide tube 606 may prevent a potentially hazardous situation to the patient and/or the user of the system while a sharp instrument is engaged in guide tube 606.

Sensor 902 may be configured such that it detects the presence of an instrument in guide tube 606. As shown in FIGS. 9A and 9B, sensor 902 may be embedded in an upper portion of guide tube 606. Sensor 902 may be a Hall effect sensor using magnetic properties of the instrument to detect the instrument's presence in guide tube 606. Sensor 902 may be covered by sensor cover 904 as shown in FIGS. 9A and 9B.

Sensor 902 may detect the instrument's presence in guide tube 606. By way of example and in no way intended to limit the manner in which the sensor may be implemented, sensor 902 may be a capacitive or resistive sensor which uses changes in the electrical properties of guide tube 606, such as its impedance, when an instrument is present in guide tube 606. Further, sensor 902 may be a mechanical switch, such as an actuated or strain gauge. Further still, sensor 902 may be an optical sensor to determine the presence of an instrument in guide tube 606. In addition, sensor 902 may be an inductive sensor that uses magnetic field changes to determine the presence of an instrument in guide tube 606.

Sensor 902 may be configured to send a signal (sensor signal) to circuitry associated with the surgical robot system. Once the surgical robot system receives such a sensor signal, surgical robot system may restrict or prevent movement of robot arm 604 while an instrument is inside guide tube 606.

In a further embodiment, the surgical robot system may also disable tracking markers 702 in response to the sensor signal. This disabling response would prevent the undesirable situation of optical interference and partial occlusion from tracking markers 702, particularly if tracking markers are light-emitting diodes.

FIGS. 10A and 10B illustrate a top view of end-effector 602 while instrument assembly 802 is inside guide tube 606 consistent with some example embodiments. End-effector 602 may further comprise spring 1002 and ball detent 1004, both of which may be disposed in or near guide tube 606. FIGS. 10A and 10B also depict outer sleeve 806 and grooves 808.

Figure 13:
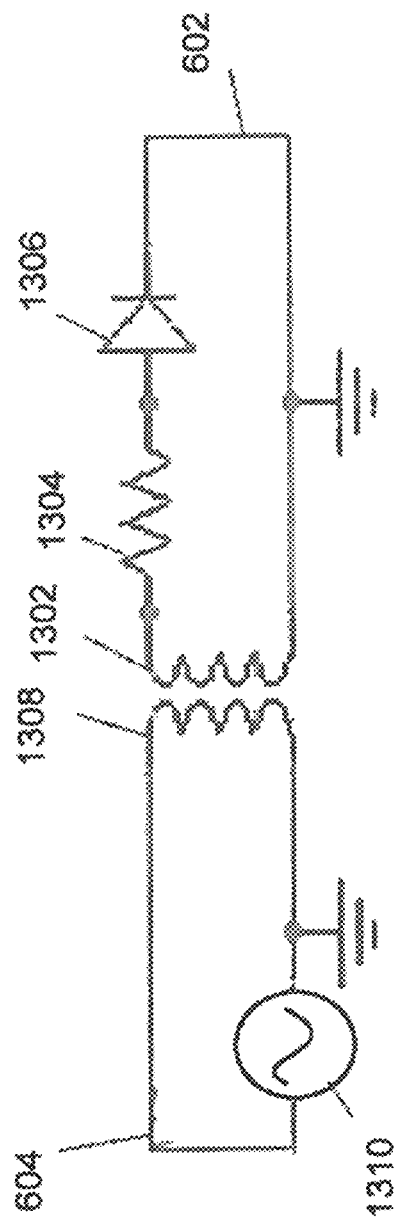
FIG. 13 illustrates portions of an end-effector and robot arm according to some example embodiments.

Instrument 608 may be disposed within instrument assembly 802 as described with respect to FIG. 13. While instrument 608 is disposed in instrument assembly 802, instrument assembly 802 may be inserted in guide tube 606. Guide tube 606 may restrict the movement of instrument assembly 802 in a manner such that tracking array 612 remains in essentially the same orientation relative to robot arm 604 and robot base 610 so that tracking devices can display the location of instrument assembly 802 on, for example, display 110. Instrument 608 may be free to rotate about its shaft without affecting rotation of the array and may move in a direction consistent with trajectory 614.

Specifically, instrument assembly 802 (after instrument 608 is inserted therein), may be inserted into guide tube 606. Structures on tip 810 of outer sleeve 806 may cause one of grooves 808 to line up and engage with ball detent 1004. Ball detent 1004 may be in communication with spring 1002 such that when a force is applied to ball detent 1004, it is able to move backward against spring 1002 and when the force is removed spring 1002 moves ball detent 1004 in a forward direction. When ball detent 1004 engages a groove 808 it may move forward into that groove 808 and spring 1002 may apply sufficient force on ball detent 1004 so that ball detent 1004 is biased towards that groove 808. With ball detent 1004 lined up and engaged with one of grooves 808, instrument assembly 802 is inserted further into guide tube 606. FIG. 10B depicts a groove 808 engaged with ball detent 1004.

Instrument 608 may freely rotate about its shaft and move along the path of trajectory 614 within instrument assembly 802. Instrument assembly 802 may be restricted from rotating within guide tube 606 while a groove 808 is engaged with ball detent 1004. The rotational position of instrument assembly 802 within guide tube 606 may be chosen such that tracking array 612 is adequately visible to the tracking devices in order to properly display the position of instrument 608 on, for example, display 110 of the surgical robot system.

While rotational movement of instrument assembly 802 inside guide tube 606 may be restricted, the rotational position of instrument assembly 802 may be adjusted. For example, instrument assembly 802 may be adjusted so that tracking array 612 is in a better position to be visible by the tracking devices. In some example embodiments, sufficient rotational force may be applied to instrument assembly 802 to disengage ball detent 1004 from a groove 808. Ball detent 1004 may move backwards upon disengaging with a groove 808. This disengagement is depicted in FIG. 10A. Once disengaged, the rotational position of instrument assembly 802 may be adjusted so that ball detent 1004 moves forward and engages a different groove 808.

Ball detent 1004 and the one or more grooves 808 may be configured such that movement along the path of trajectory 614 is not restricted. This configuration may allow instrument assembly 802 to move along a path of trajectory 614, while guide tube 606 restricts rotational movement of instrument assembly 802 to maintain a fixed orientation of tracking array 612 in relation to the tracking devices.

Ball detent 1004 has been described in relation to spring 1002 and being a spring plunger type of structure. However, it is understood that other structures may be used to restrict rotational movement of instrument assembly 802 in guide tube 606 in order to maintain an orientation of tracking array 612. For example, such structures may include and are not limited to a coil spring, wave spring, flexure, torsional spring mounted to a lever, or a compressible material. Further, ball detent 1004 and spring 1002 have been described as being part of guide tube 606, however, ball detent 1004 and spring 1002 may be disposed on instrument assembly 802 and engage with complimentary mechanisms associated with end-effector 602 or guide tube 606 to similarly restrict the rotation movement of instrument assembly 802.

Figure 11:
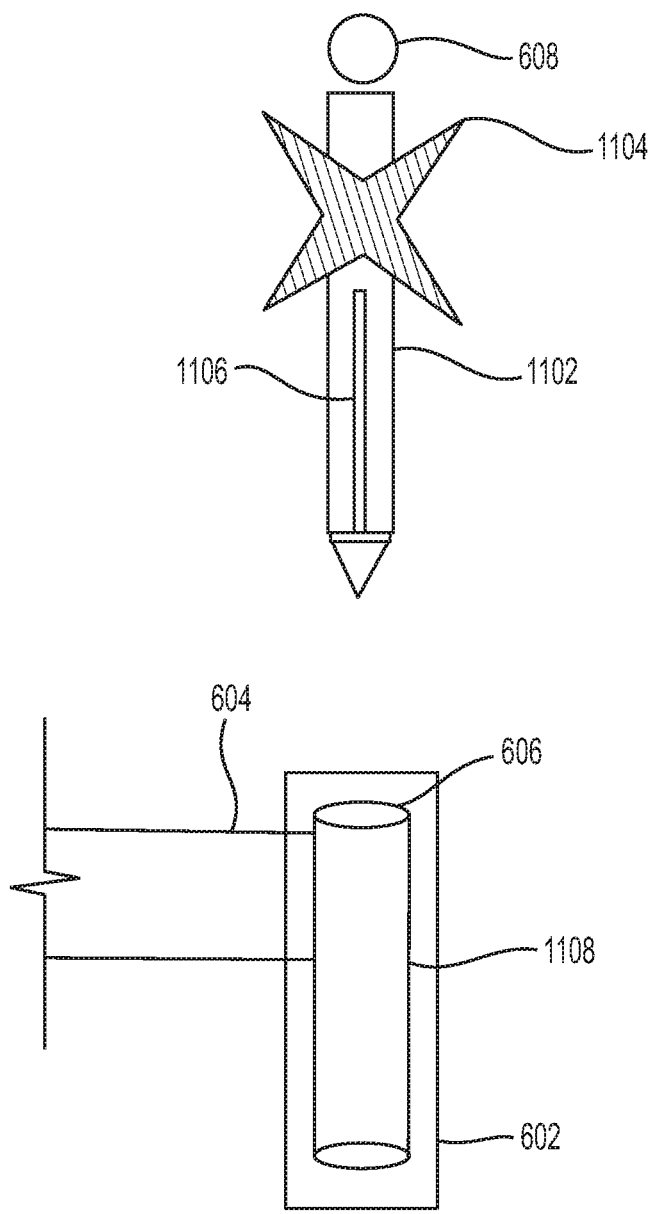
FIG. 11 illustrates an instrument and guide tube according to some example embodiments.

FIG. 11 illustrates end-effector 602, instrument 608, instrument assembly 1102, tracking array 1104, and guide tube 606 consistent with in some example embodiments. Instrument assembly 1102 may further comprise groove 1106. Guide tube 606 may further comprise channel 1108.

As described previously, rotational movement of instrument assembly 802 may be restricted when it is received by guide tube 606. In some example embodiments, to restrict movement of an instrument assembly while inside a guide tube, instrument assembly 1102 may have groove 1106 configured to engage channel 1108 of guide tube 606 to similarly restrict rotational movement of instrument assembly 1102 when received by guide tube 606. Once groove 1106 is engaged with channel 1108, instrument assembly 1102 is restricted from rotating about its shaft axis while instrument assembly 1102 is inside guide tube 606.

Other methods and components may be used to restrict the rotational movement of an instrument assembly while inside a guide tube. For example, one or more cylindrical rollers may be used that is configured with roller axis perpendicular to the instrument shaft to roll and allow for axial movement of an instrument assembly along the path of trajectory 614 but is configured to remain stationary when attempts are made to rotationally move instrument assembly within guide tube 606. This configuration would have the effect of fixing the orientation of tracking array 612. The roller may be made of a flexible material and held rigidly protruding into guide tube 606 to engage with an outer sleeve of the instrument assembly. The roller may also be made of a rigid material and spring loaded, pushing into guide tube 606 to engage with the instrument assembly. Moreover, the roller may be disposed on an instrument assembly and engage guide tube 606 when the instrument assembly is inserted into guide tube 606.

In some example embodiments, rotation of an outer sleeve of instrument assembly may be restricted from rotating but allowing for axial movement through the use of anisotropic surface textures for the outer sleeve and guide tube 606. This texture pattern may allow for different friction forces associated with rotation of the outer sleeve and axial movement so that a user may need to apply a relatively higher force to rotationally move the instrument assembly compared to moving the instrument assembly in an axial direction consistent with trajectory 614.

Figure 12:
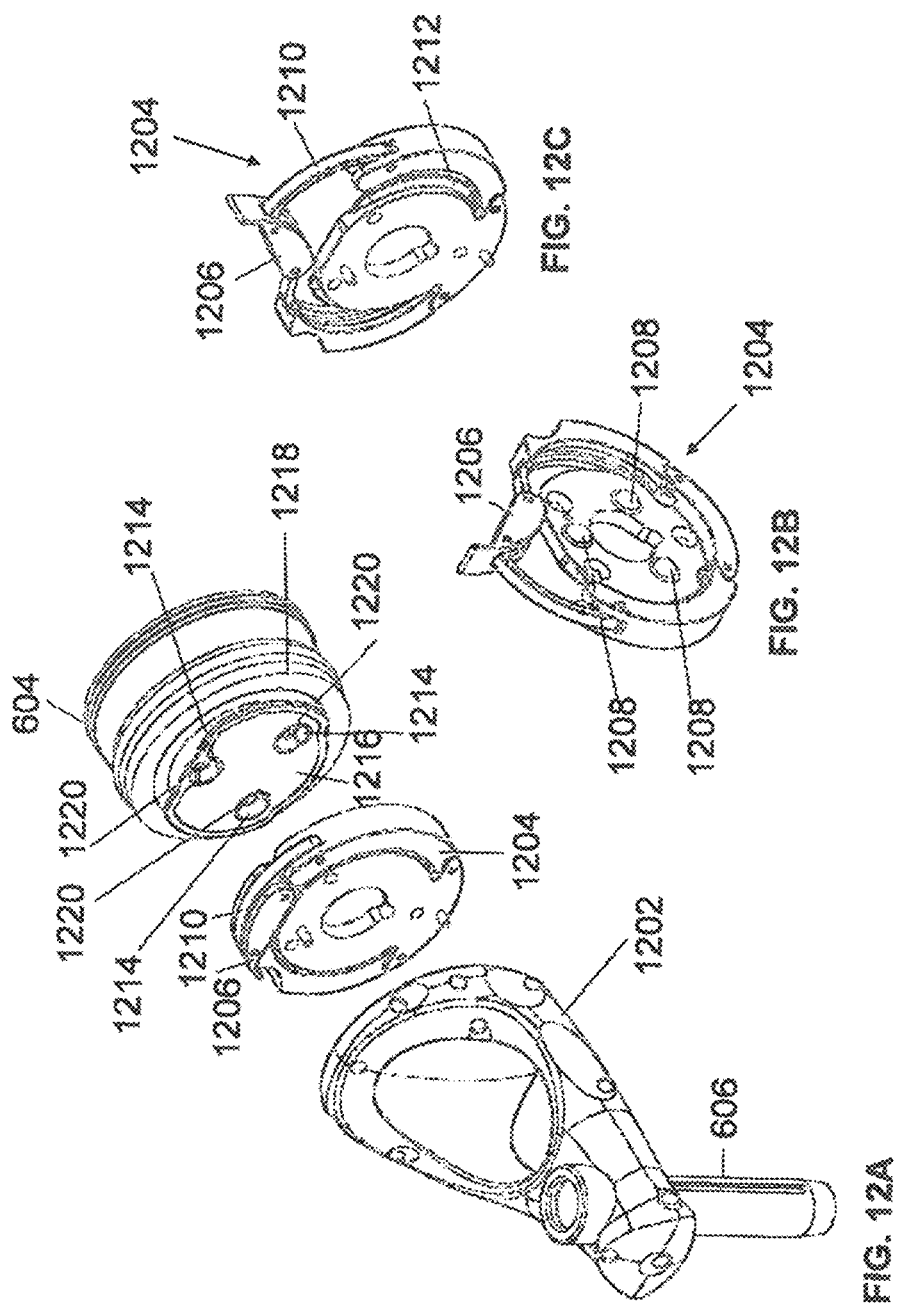
FIGS. 12A-12C illustrate portions of an end-effector and robot arm according to some example embodiments.

FIGS. 12A-12C illustrate end-effector 602 and a portion of robot arm 604 consistent with in some example embodiments. End-effector 602 may further comprise body 1202 and clamp 1204. Clamp 1204 may comprise clamp handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In some example embodiments, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 12B would be seated in depressions 1214 as shown in FIG. 12A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (poly-ether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 602 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

FIG. 13 is a circuit diagram that illustrates power transfer between end-effector 602 and robot arm 604 consistent with some example embodiments. End-effector 602 may comprise a coil 1302, resistor 1304, and diode 1306. Robot arm 604 may comprise coil 1308 and voltage supply 1310.

End-effector 602 and robot arm 604 may be configured in a manner to allow for wireless power transfer in order to power end-effector 602 and components associated with end-effector 602. In some example embodiments, end-effector 602 may comprise coil 1302 that receives an electromagnetic field generated by robot arm 604. Robot arm 604 may contain coil 1308, which may serve as a primary coil in an inductive power transfer system between robot arm 604 and end-effector 602 over an air gap. In some example embodiments, the air gap may be in the range of 0.1 mm to 20 mm. Coil 1308 may be coupled to voltage supply 1310 in order to generate the electromagnetic field. The electromagnetic field may be received by coil 1302 of end-effector 602 to generate an electrical current.

The inductive power relationship between may power components of end-effector 602 such as tracking markers 702, sensor 902, and other electrical components associated with end-effector 602. By providing wireless powering, end-effector 602 may be physically and/or electrically isolated from robot arm 604 while powering electronics and other components contained in end-effector 602.

The resistance of resistor 1304 may be varied among a number of distinct states, causing differential power draw. The power draw may be measured from the side of the surgical robot as a means of wirelessly passing a signal from end-effector 602 to the surgical robot base 610. Alternatively, a battery could be used to power the electronics, and a standard wireless communications protocol such as Bluetooth may be used to exchange signals between end-effector 602 and robot base 610. Data transferred to robot base 610 may include state information. This information may include a determination of whether end-effector 602 is detached from robot arm 604, and if instrument 608 is present in guide tube 606.

The power transmission between robot arm 604 and end-effector 602 may be based on electromagnetism, optics, or ultrasound. For each of these transmission types, the corresponding resistance on end-effector 602 can be varied to communicate the state of end-effector 602. End-effector 602 may propagate power or receive one or more signals by any of the aforementioned principles to other items in the sterile field, such as drills, screw drivers, implant holders, or lights. In addition, power and/or signal may be passed to other sterile items via a contact connection.

Figure 14:
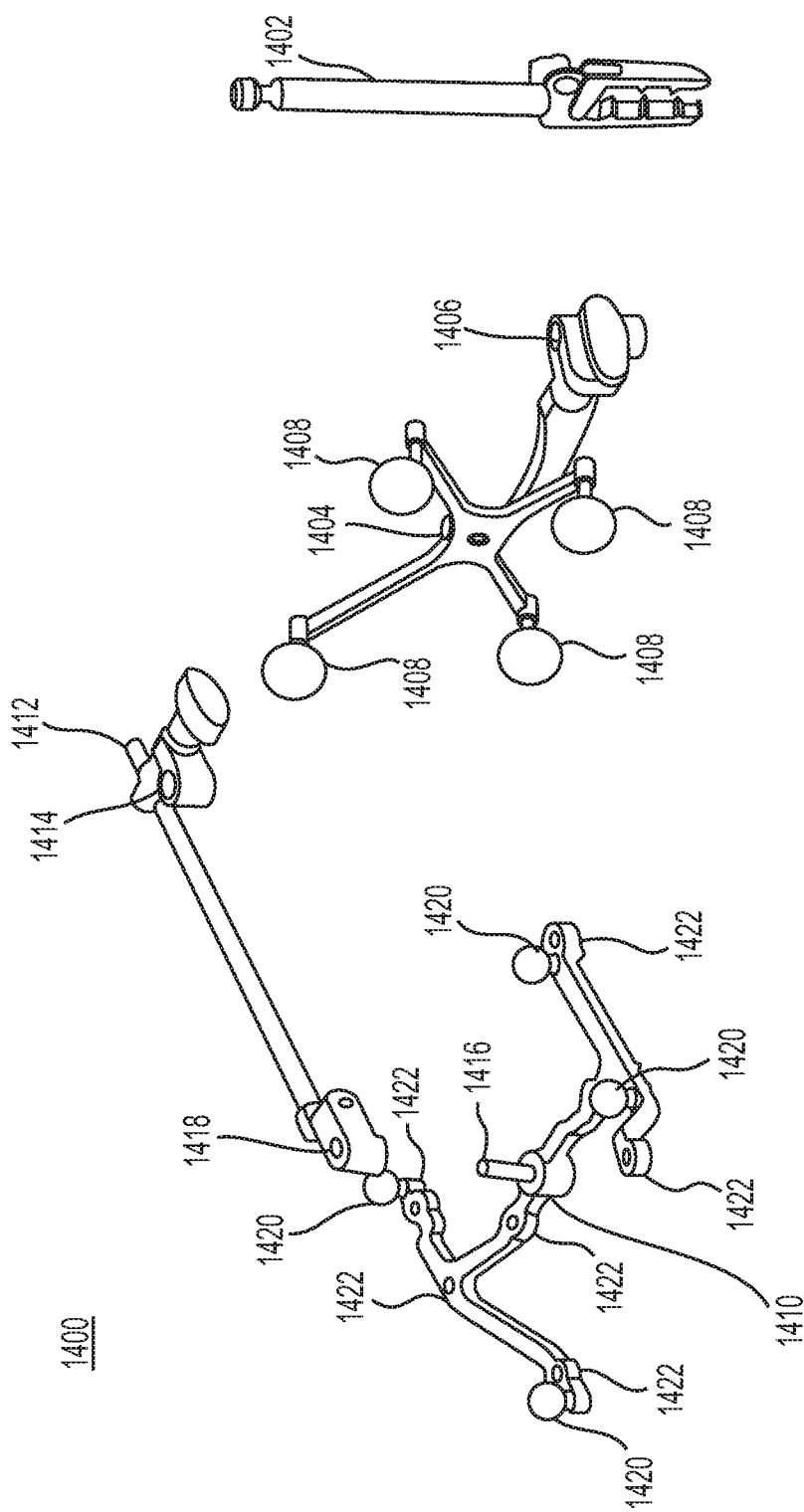
FIG. 14 illustrates a dynamic reference array, an imaging array, and other components according to some example embodiments.

Referring to FIGS. 14 and 15, prior to or during a surgical procedure, certain registration procedures may be conducted in order to track objects and a target anatomical structure of the patient both in a navigational space and an imaging space. In order to conduct such registration, registration system 1400 may be used as illustrated in FIG. 14.

Patient fixation instrument 1402 may be secured to a rigid anatomical structure of the patient and dynamic reference base (DRB) 1404 may be attached to patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers may be optical markers or reflective spheres as previously discussed herein.

Patient fixation instrument 1402 is attached to a rigid anatomy of the patient and may remain attached throughout the surgical procedure. In some example embodiments, patient fixation instrument 1402 is attached to a rigid area of the patient, for example a bone, that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an imaging space and navigational space using tracking markers or fiducials on registration fixture 1410. Registration fixture 1410 may contain a collection of markers 1420 that are visible in a navigational space (for example, markers 1420 may be detectable by tracking subsystem 532). Markers 1420 may be optical markers visible in infrared light as previously described herein. Registration fixture 1410 may also contain a collection of fiducials 1422 (e.g., ball bearings) that are visible in an imaging space (for example, a three-dimension CT image). As described in greater detail with respect to FIG. 15, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 15 provides method 1500 for registration consistent with some example embodiments. Method 1500 begins at step 1502 wherein a graphical representation (or image(s)) of the targeted anatomical structure may be imported into surgical robot system 300, for example computer 408. The graphical representation may be three-dimensional CT or a fluoroscope scan of the targeted anatomical structure of the patient which includes registration fixture 1410 and a detectable imaging pattern of fiducials 1422.

At step 1504, an imaging pattern of fiducials 1422 is detected and registered in the imaging space and stored in computer 408. Optionally, at this time at step 1506, a graphical representation of registration fixture 1410 may be overlaid on the images of the targeted anatomical structure.

At step 1508, a navigation pattern of registration fixture 1410 is detected and registered by recognizing markers 1420. Markers 1420 may be optical markers that are recognized in the navigational space through infrared light by tracking subsystem 532 via position sensor 540. Thus, the location, orientation, and other information of the targeted anatomical structure is registered in the navigational space. Therefore, registration fixture 1410 may be recognized in both the imaging space through the use of fiducials 1422 and the navigational space through the use of markers 1420. At step 1510, the registration of registration fixture in the imaging space is transferred to the navigational space. This transferal is done, for example, by using the relative position of the imaging pattern of fiducials 1422 compared to the position of the navigation pattern of markers 1420.

At step 1512, registration of the navigational space of registration fixture 1410 (having been registered with the imaging space) is further transferred to the navigational space of dynamic reference base 1404 attached to patient fixation instrument 1402. Thus, registration fixture 1410 may be removed and dynamic reference base 1404 may be used to track the targeted anatomical structure in both the navigational space and the imaging space because the navigational space is associated with the imaging space.

At steps 1514 and 1516, the navigational space may be overlaid on the imaging space and objects with markers visible in the navigational space (for example, surgical instruments with optical markers). The objects may be tracked through graphical representations of the surgical instrument on the images of the targeted anatomical structure.

Figure 16:
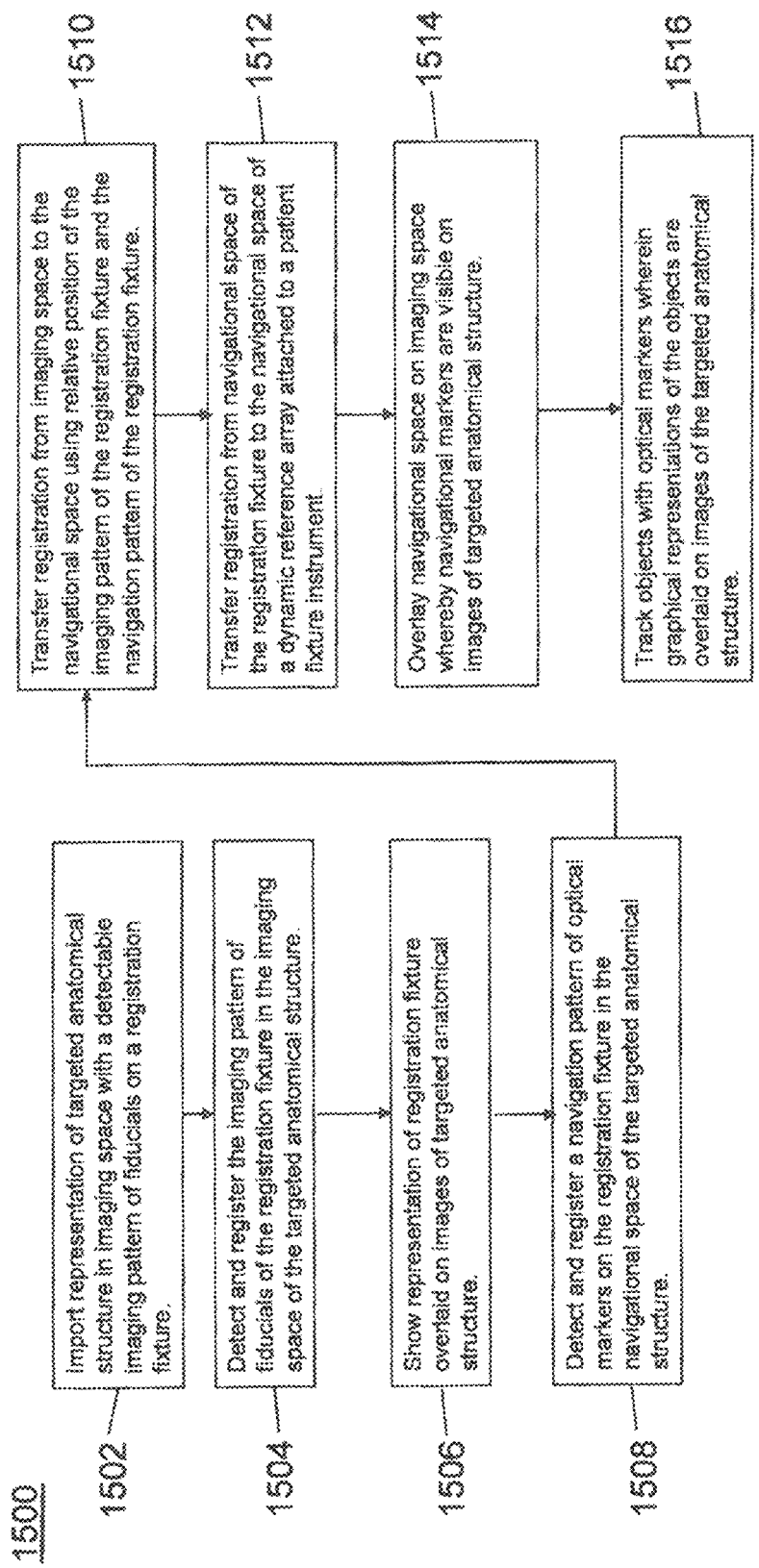
FIGS. 16A and 16B illustrate imaging systems according to some example embodiments.
Figure 16A:
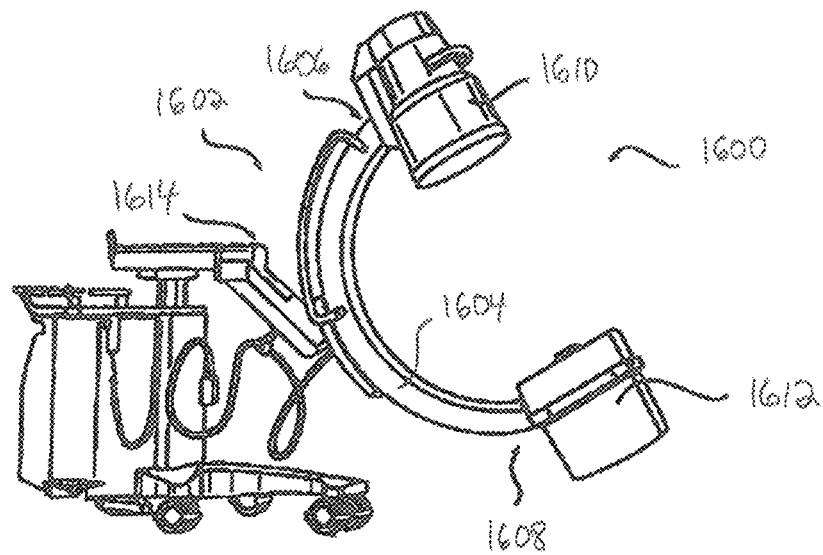
Figure 16B:
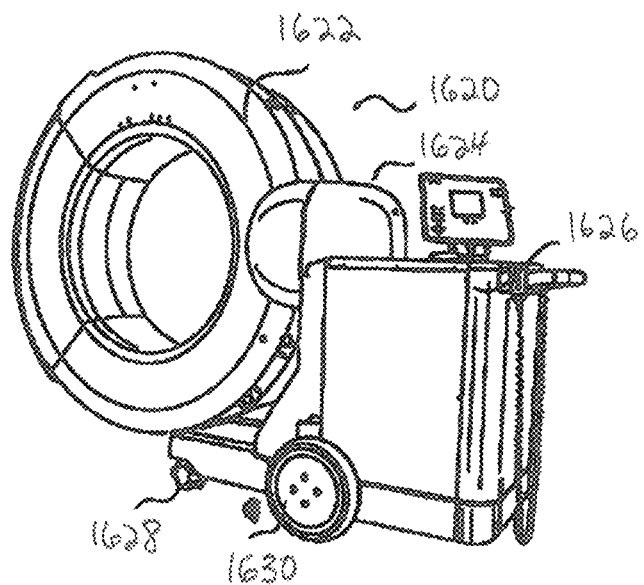

FIGS. 16A and 16B illustrate imaging systems according to some example embodiments that may be used in conjunction with surgical robot systems 100, 300, 600 to acquire pre-operative, intra-operative, post-operative, and/or real-time image data of patient 210. It may be desirable to take X-rays of patient 210 from a number of different positions, without the need for frequent manual repositioning of patient 210, which may be required in a typical X-ray system. FIG. 16A illustrates C-arm imaging device 1600, comprising C-arm 1602 that includes an elongated C-shaped member 1604 terminating in opposing distal ends 1606, 1608 of the "C" shape. C-arm imaging device 1600 may further comprise X-ray source 1610 and image receptor 1612 on C-shaped member 1604. The space within C-arm 1602 may provide room for a physician to attend to patient 210 substantially free of interference from X-ray support structure 1614. FIG. 16B illustrates O-arm imaging device 1620, comprising gantry housing 1622 attached to imaging device support structure 1624, such as mobile cart 1626 with wheels 1628, 1630. O-arm imaging device 1620 may enclose an image capturing portion (not illustrated). The image capturing portion may include an X-ray source and/or emission portion and an X-ray receiver and/or image receptor portion, which may be disposed about one hundred and eighty degrees from each other and mounted on a rotor (not illustrated) relative to a track of the image capturing portion. The image capturing portion may be operable to rotate 360° during image acquisition. The image capturing portion may rotate around a central point and/or axis, allowing image data of patient 210 to be acquired from multiple directions or in multiple planes. Although FIGS. 16A and 16B illustrate imaging systems that include C-arm imaging device 1600 and O-arm imaging device 1620, it will be appreciated that any suitable imaging system may be selected by one of ordinary skill in the art.

Imaging systems that include C-arm imaging device 1600 and O-arm imaging device 1620 may be used, for example, for intra-operative registration of a 3D imaging space of a surgical system with a 3D tracking space of the surgical system. As would be understood by one of ordinary skill in the art, pre-operative registration of the 3D imaging space of a surgical system with a 3D tracking space of the surgical system may be accomplished through several approaches, such as point-matching registration, point-cloud registration, and/or fluoroscopic registration.

Turning now to FIGS. 17A-23, as previously discussed, CT-assisted robotic or non-robotic surgical navigation requires the CT image volume to be registered with the camera (or navigation) space so that a position of a tracked tool is known relative to the anatomy by using optical, electromagnetic or other tracking devices (for example, Polaris Spectra, Northern Digital, Inc., Waterloo, Ontario, Canada). After successful registration, at any frame of tracked data, the surgical navigation system records the tracked position of a dynamic reference base (DRB) that is affixed to the patient and records the tracked position of any tool that is in the field of view of the cameras. The system then performs a transformation to use the position data for the location of the tool and patient in the tracking camera's coordinate system to display a graphic representation of the tool in the medical image coordinate system.

Systems, methods, and devices that may be used for performing registration of an intraoperative CT image (for example, from an O-arm) to tracking or navigation cameras using radio-opaque fiducials detected in the CT image and optical tracking markers at a known relative position to the radio-opaque fiducials that are simultaneously tracked have been previously described as noted above. It may also be possible to register a preoperative CT coordinate system or image to the optical or navigation tracking coordinate system through other methods.

Consistent with the present disclosure, an intraoperative fluoroscopic x-ray imaging system, such as a C-arm, may be used after registration of the CT image to the tracking or navigation system has been performed. An intraoperative fluoroscopy unit may be positioned to take one or more x-ray images of the patient and this fluoroscopy unit may also have a tracking fixture attached to an image intensifier. Such a tracked registration fixture may be those as described above and may also comprise an array of bearing balls ("bbs") arranged in different planes from one another, concentric rings in different planes, or other markings that are detectable in the x-ray image and allow registration of the x-ray image space to the camera space.

Due to the nature of fluoroscopic x-ray images being two-dimensional, even with a fluoroscopy registration fixture, it may be very difficult or impossible to establish a mathematical transformation such that a particular point seen on a single x-ray image corresponds to a unique point in 3D space. This lack of uniqueness may be due to inability to precisely know how far away from an image plane in 3D space a point projected on the 2D image is located.

Consistent with the principles of the present disclosure, a particular point in a single 2D image may be used to precisely quantify the location of an infinite vector along which that point on the 2D image must be located.

FIGS. 17A and 17B illustrate imaging systems according to some example embodiments.

FIG. 17A illustrates X-ray source 1700 (treated as a point source) and image intensifier 1702. FIG. 17A shows a projection of a point(s) appearing on an x-ray image. A mapping of the paths of X-rays emitted by X-ray source 1700 and received at image intensifier 1702 would appear conical. FIG. 17A also illustrates radio-opaque points 1704, 1706; and projections 1708, 1710. X-rays emitted by X-ray source 1700 toward radio-opaque point 1704 would create a shadow effect on image intensifier 1702 at projection 1708. Similarly, X-rays emitted by X-ray source 1700 toward radio-opaque point 1706 would create a shadow effect on image intensifier 1702 at projection 1710. If a point appearing on the x-ray is exactly in the center of the x-ray image, the vector is a line through the center of the image and exactly perpendicular to the x-ray projection plane. If the point is lateral to the center of the image, the vector becomes less perpendicular to the image plane and matches the conical dispersion of x-rays leaving the emitter and traveling toward the collector.

FIG. 17B illustrates X-ray source 1720 (treated as a point source), image intensifier 1722, tracking fixture 1724, and tracking array 1726. A mapping of the paths of X-rays emitted by X-ray source 1720 and received at image intensifier 1722 would appear conical. FIG. 17B also illustrates first radio-opaque points 1728, 1730, 1732, 1734; second radio-opaque points 1736, 1738, 1740, 1742; first projections 1744, 1746, 1748, and 1750; and second projections 1752, 1754, 1756, and 1758. X-rays emitted by X-ray source 1720 toward first radio-opaque points 1728, 1730, 1732, 1734 would create respective shadow effects on image intensifier 1722 at first projections 1744, 1746, 1748, and 1750. Similarly, X-rays emitted by X-ray source 1720 toward second radio-opaque points 1736, 1738, 1740, 1742 would create respective shadow effects on image intensifier 1722 at second projections 1752, 1754, 1756, and 1758.

In FIG. 17B, tracking fixture 1724 may be, for example, a block of radiolucent material including an array of radio-opaque objects (e.g., bearing balls) at first radio-opaque points 1728, 1730, 1732, 1734 and/or second radio-opaque points 1736, 1738, 1740, 1742. The array may be, for example, a 3D array. The 3D array may include two or more planes which have multiple radio-opaque objects in each plane. The planes may be a known distance apart. The radio-opaque objects in each plane may be ordered in a pattern. The pattern may be the same or different in each plane. As would be understood by one of ordinary skill in the art, the use of different patterns in different planes a known distance apart may simplify geometric analysis for determining the relative location and/or orientation of X-ray source 1720, image intensifier 1722, tracking fixture 1724, and/or tracking array 1726.

The radio-opaque objects at any given radio-opaque point may be of the same or different size as those of any other radio-opaque point. In FIG. 17B, the shadow effects on image intensifier 1722 at first projections 1744, 1746, 1748, and 1750 appear larger than the shadow effects on image intensifier 1722 at second projections 1752, 1754, 1756, and 1758. As would be understood by one of ordinary skill in the art, the size of the shadow effects on image intensifier 1722 may be influenced by a first distance between X-ray source 1720 and a particular radio-opaque object, the radio cross-section of the particular radio-opaque object, and a second distance between the particular radio-opaque object and intensifier 1722. As would be understood by one of ordinary skill in the art, the use of radio-opaque object of different radio cross-sections may simplify geometric analysis for determining the relative and/or absolute locations and/or orientations of X-ray source 1720, image intensifier 1722, tracking fixture 1724, and/or tracking array 1726.

In FIG. 17B, tracking array 1726 includes a plurality of tracking markers 1760. Tracking markers 1760 allow the determination of the relative and/or absolute locations and/or orientations of tracking fixture 1724 and/or tracking array 1726. If tracking fixture 1724 is attached to image intensifier 1722, tracking markers 1760 also allow the determination of the relative location and/or orientation of image intensifier 1722. If tracking fixture 1724 is not attached to image intensifier 1722, an additional tracking array attached to image intensifier 1722 may be provided (not shown).

As would be understood by one of ordinary skill in the art, X-ray imaging systems such as X-ray source 1720, image intensifier 1722, tracking fixture 1724, and tracking array 1726 may allow pre-operative and intra-operative registration of imaging systems, such as C-arm imaging device 1600 and/or O-arm imaging device 1620, with registration system 1400 (e.g., dynamic reference base 1404 and/or registration fixture 1410). Thus, use of tracking array 1726 (or the additional tracking array) may allow registration of an X-ray imaging space of the associated X-ray imaging system to a 3D tracking space (e.g., navigational space) of a surgical system.

Consistent with the present disclosure, after taking a single x-ray of the patient, such as a lateral or anteroposterior x-ray, while tracking the registration fixture on, for example, the C-arm and the DRB on the patient, a point on the x-ray image may be mapped to a 3D infinite vector in the coordinate system of the cameras. Recording the position of the DRB may also enable the camera coordinate system to shift with the patient if there is patient movement, allowing this mapping to remain valid relative to the patient. One possible manner for creating such a map of points on the x-ray to corresponding vectors is to use bbs on the registration fixture to generate a set of vectors, as shown in FIG. 17B, and then to interpolate between these vectors for any point identified on the x-ray plane (for example, a point of interest) other than the points creating shadows on the x-ray. Once the X-ray imaging space of the X-ray imaging system is registered to the 3D tracking space, 2D X-ray images may be obtained by the X-ray imaging system that correspond to the 3D tracking space. Then, a point of interest may be identified in the 2D X-ray image, the 3D imaging space, or the 3D tracking space. The point of interest may be identified, for example, by an operator of an associated surgical system or by a processor of the surgical system (using, for example, a software-based tool). The point of interest may be, for example, a point on or within patient 210. The point of interest on or within patient 210 may be mapped to the 2D X-ray image. The point of interest may be shown, for example, on a display of the surgical system.

Being able to map any point on the 2D x-ray image to a corresponding infinite 3D vector in terms of the tracker's coordinate system, a software-based tool used by the robot system may check a previous 3D registration. To use this tool, the user may select a point on the x-ray image that is meaningful (a point of interest), such as the tip of a bony process. The robot system may be able to construct the infinite vector in 3D space on which the point of interest lies. Since the 3D medical image space is registered to the navigation tracking cameras, the vector may be displayed on the 3D medical image and shown to the user on a computer monitor. The user may verify or inspect the displayed 3D medical image to ensure that the vector crosses the anatomy of interest at the correct location (in other words, check to determine if the 3D infinite vector passes through the point of interest). If the vector does not correctly traverse the 3D image volume, this discrepancy may indicate a registration error. Offset of this vector laterally from its expected intersection may be easily and accurately measured since the 3D medical image volume space may be well calibrated with a well-defined number of voxels per millimeter. This accurate calibration may be particularly true in relation to the 2D x-ray, as the x-ray scaling may not be as well defined as the 3D image volume scaling, thus, a quantitative estimate of the offset may be more easily obtained from the 3D medical image volume space. However, any vertical offset along the vector in the 3D tracking space may be undefined. For at least these reasons, it is advantageous for a user of the surgical system to orient the imaging system (e.g., C-arm imaging device 1600) so that it tends to reveal the most important offsets. For example, if the surgical operation involves placing a bone screw, it may be less important to preliminarily determine that the screw reaches a target depth as opposed to knowing that the screw is inserted in the correct entry point. If the x-ray is oriented such that it aims down the path of the screw, then the vector generated in 3D will run approximately parallel to the path of the screw, and any offset seen between 2D and 3D relative to a targeted anatomical point will represent how much error would be expected laterally rather than longitudinally in the navigated screw.

As an example, a user may obtain an intraoperative CT with a registration fixture in order to perform CT-to-tracking system registration. After the CT is obtained, the CT image volume is searched and fiducial locations of the registration fixture are identified. From known relative positions of the tracked markers on the registration fixture, the transformation between CT image volume coordinate system and tracking coordinate system may be established. After registering, the transformation is reassigned to be relative to the DRB on the patient so that the tracking coordinate system is based on the patient position, not the fixed camera position.

Further to this example, after registration is established and during surgery, a user may want to later verify that the accuracy of the registration was still accurate. Loss of accuracy may arise when the DRB is bumped so that its position is off from the intended position, for example shifted by 10 mm toward the anatomical left of the patient. If an anteroposterior x-ray is then taken with a fluoroscopic registration fixture attached to the c-arm and a point on the tip of the spinous process is identified, the 3D vector going through this point can be constructed using the tool described above. This vector may be with respect to the cameras and relative to the DRB in its current shifted location. However, the transformation from camera coordinates to 3D image volume coordinates used by the 3D registration sees this vector only as a vector in 3D space and is not in relation to the actual position of the patient anatomy. After processing the vector through the transformation and displaying the vector on the 3D image volume, the vector would intersect the anatomy at a location about 10 mm toward anatomical right of the patient's spinous process, and it would be clear that there was a registration error.

Figure 18:
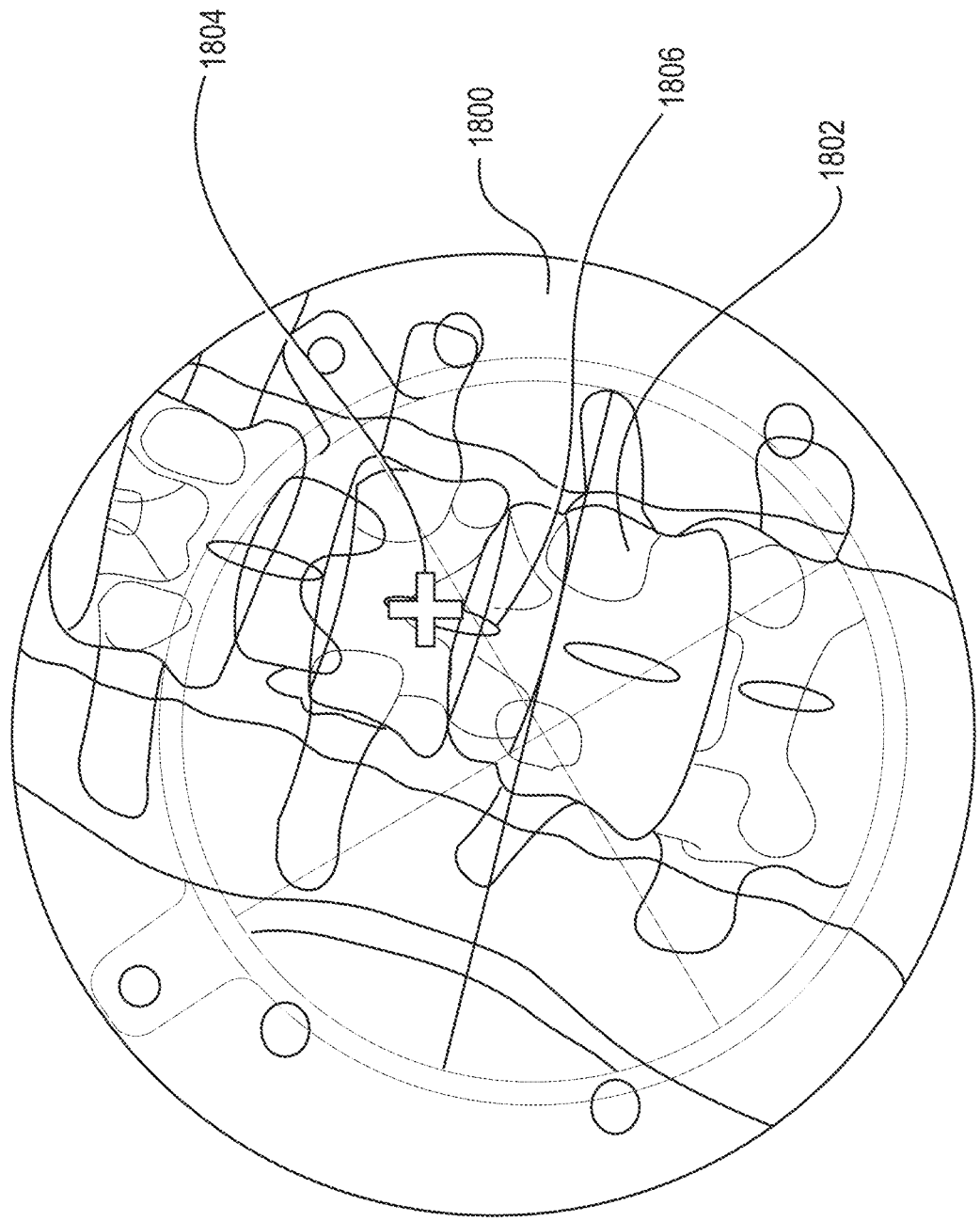
FIG. 18 illustrates a 2D X-ray image according to some example embodiments.

Checking the accuracy of the registration may be done by the user to identify through software interactions where the point of interest is located on the 2D x-ray image. In other words, the user may point to a location on the x-ray image via touchscreen or mouse, then click the mouse or lift their finger off the touchscreen to select the point. The system would then perform calculations and display on the 3D image volume where the vector through the point is located (for example, FIG. 18 as described in greater detail below). Alternately, the user could hold a tracked tool and move the tool around relative to the tracking cameras. The system could track the location of a point on the tool, such as the tool tip, map this point to the 2D x-ray image, and display it on the 2D x-ray image while simultaneously displaying the corresponding vector on the 3D image volume. As an example, the user could be touching the surface of the skin on the patient's back with a tracked probe and watching the computer screen to see how this point manifests as a projection on the 2D image and a vector on the 3D image volume. FIG. 18 illustrates a 2D X-ray image according to a some example embodiments. 2D X-ray image 1800 shows spinal column 1802 of patient 210, with a "+" mark 1804 indicating a spinous process 1806. A vector in a 3D tracking space that passes through "+" mark 1804 may be determined.

Figure 19A:
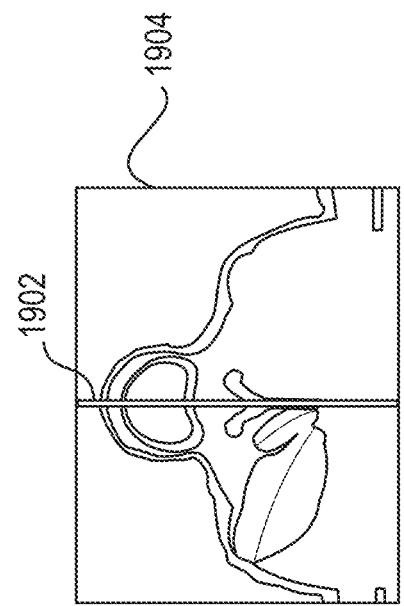
FIGS. 19A-19D illustrate four views of a 3D imaging space according to some example embodiments.
Figure 19B:
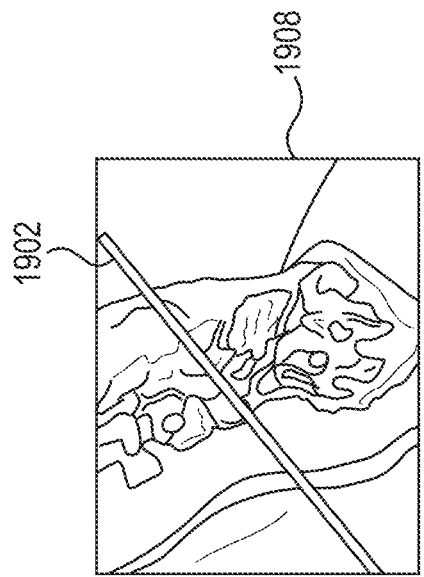
Figure 19C:
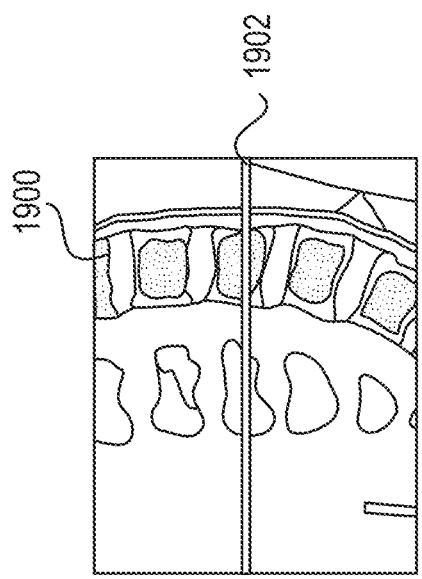
Figure 19D:
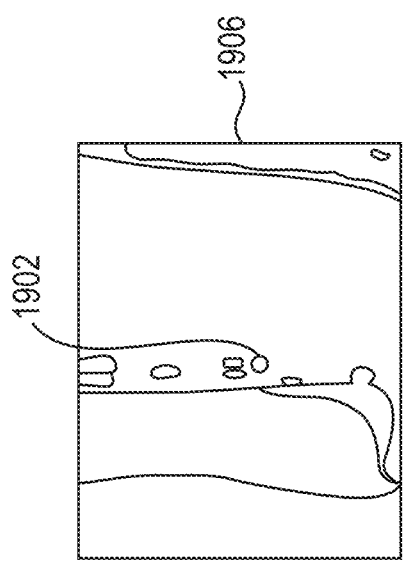

FIGS. 19A-19D illustrate four views of a 3D imaging space according to some example embodiments. FIG. 19A illustrates left-side view 1900 of vector 1902 in the 3D tracking space that passes through "+" mark 1804. FIG. 19B illustrates top or bottom view 1904 of vector 1902 in the 3D tracking space that passes through "+" mark 1804. FIG. 19C illustrates anterior or posterior view 1906 of vector 1902 in the 3D tracking space that passes through "+" mark 1804. FIG. 19D illustrates left posterolateral perspective view 1908 of vector 1902 in the 3D tracking space that passes through "+" mark 1804. FIGS. 19A-19D show how a point of interest in the 2D x-ray image translates into a vector or line traversing through different slices of the 3D CT image volume space.

Specifically, FIGS. 19A-D show CT image volume images corresponding to the "plus" mark as a vector traversing through the spinous process. FIGS. 19A, 19B, and 19C represent mutually orthogonal slice planes of the CT image volume and show a line (vector 1902) coplanar with FIGS. 19A-B and perpendicular to FIG. 19C. FIG. 19D shows a 3D view showing vector 1902 from a posterolateral perspective of the anatomy. Consistent with principles of the present disclosure, one of ordinary skill in the art would recognize that in practice the views may be 3D in nature displayed on a computer monitor as opposed to the slices shown here.

If more than one 2D X-ray image is taken, it may be possible to map more than one vector to the 3D imaging space or the 3D tracking space. Assuming identification of the same point of interest in each of the 2D X-ray images, the vectors in the 3D tracking space would be expected to intersect in the 3D tracking space at the same point. Knowledge of such a point should allow the detection and measurement of offsets from the expected location in all directions.

In addition, as an exemplary embodiment, a point of interest may be identified in the 3D imaging space or the 3D tracking space, and this point of interest may be mapped to each of the 2D X-ray images. Based on a location of the point of interest in the 2D X-ray images, the registration of the 3D imaging space with the 3D tracking space may be evaluated by assessing how far (in pixel units) from the correct location the selected point falls.

Moreover, if more than one x-ray image has been taken and the images are taken from different perspectives, consistent with the principles of the present disclosure, a user may manipulate a point on either or both x-ray images to see how this point transforms to a point in a 3D image volume. The point, marked in both x-ray views, should fall on the corresponding point in the 3D image volume. For example, if the user manipulates a graphic object on two x-ray views such that a pointer is pointing to the midwidth, midheight tip of the spinous process from both an anterior and a lateral 2D x-ray perspective, this point can be mapped to the 3D image volume and displayed as slices through the CT image volume or perspective view of the CT image volume. The registration error can be assessed as how far in millimeters this point is from the midwidth, midheight tip of the spinous process on the 3D image volume.

Figure 20:
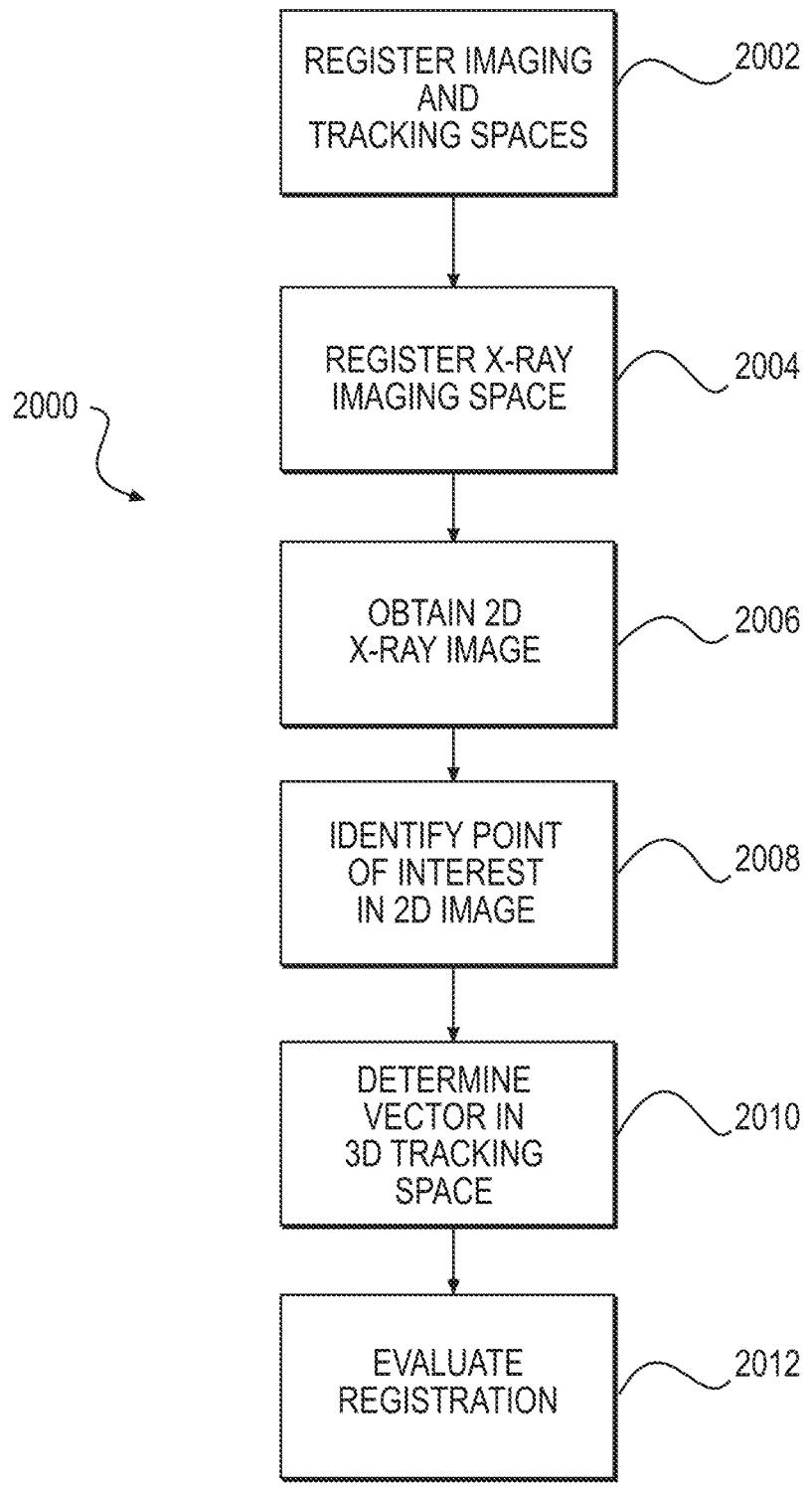
FIG. 20 illustrates a first method of checking registration for a surgical system according to some example embodiments.

FIG. 20 illustrates a first method of checking registration for a surgical system according to some example embodiments. In first method 2000 of checking registration for a surgical system, the surgical system comprising fiducials and tracking markers, method 2000 may comprise: using the fiducials and the tracking markers to register a three-dimensional (3D) imaging space of the surgical system with a 3D tracking space of the surgical system (2002); using a tracking fixture of an X-ray imaging system to register an X-ray imaging space of the X-ray imaging system to the 3D tracking space (2004); obtaining a two-dimensional (2D) X-ray image corresponding to the 3D tracking space (2006); identifying a point of interest in the 2D X-ray image (2008); determining a vector in the 3D tracking space that passes through the point of interest (2010); and/or evaluating the registration of the 3D imaging space with the 3D tracking space based on a location, an orientation, or the location and the orientation of the vector in the 3D tracking space (2012).

Figure 21:
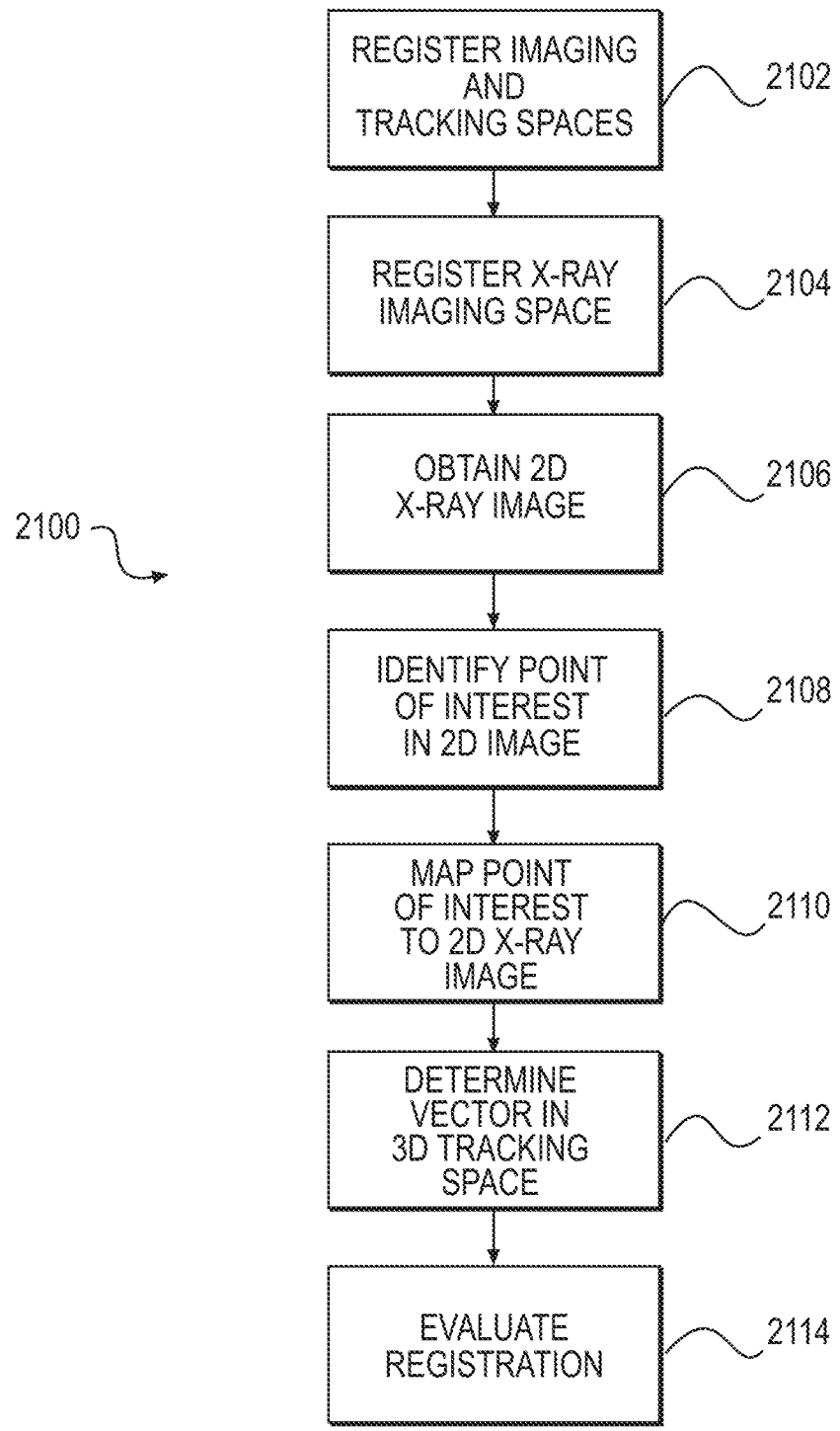
FIG. 21 illustrates a second method of checking registration for a surgical system according to some example embodiments.

FIG. 21 illustrates a second method of checking registration for a surgical system according to some example embodiments. In second method 2100 of checking registration for a surgical system, the surgical system comprising fiducials and tracking markers, method 2100 may comprise: using the fiducials and the tracking markers to register a three-dimensional (3D) imaging space of the surgical system with a 3D tracking space of the surgical system (2102); using a tracking fixture of an X-ray imaging system to register an X-ray imaging space of the X-ray imaging system to the 3D tracking space (2104); obtaining a two-dimensional (2D) X-ray image of a patient corresponding to the 3D tracking space (2106); identifying a point of interest of the patient (2108); mapping the point of interest to the 2D X-ray image (2110); determining a vector in the 3D tracking space that passes through the point of interest (2112); and/or evaluating the registration of the 3D imaging space with the 3D tracking space based on a location of the point of interest in the 2D X-ray image; a location, an orientation, or the location and the orientation of the vector in the 3D tracking space; or the location of the point of interest in the 2D X-ray image and the location, the orientation, or the location and the orientation of the vector in the 3D tracking space (2114).

Figure 22:
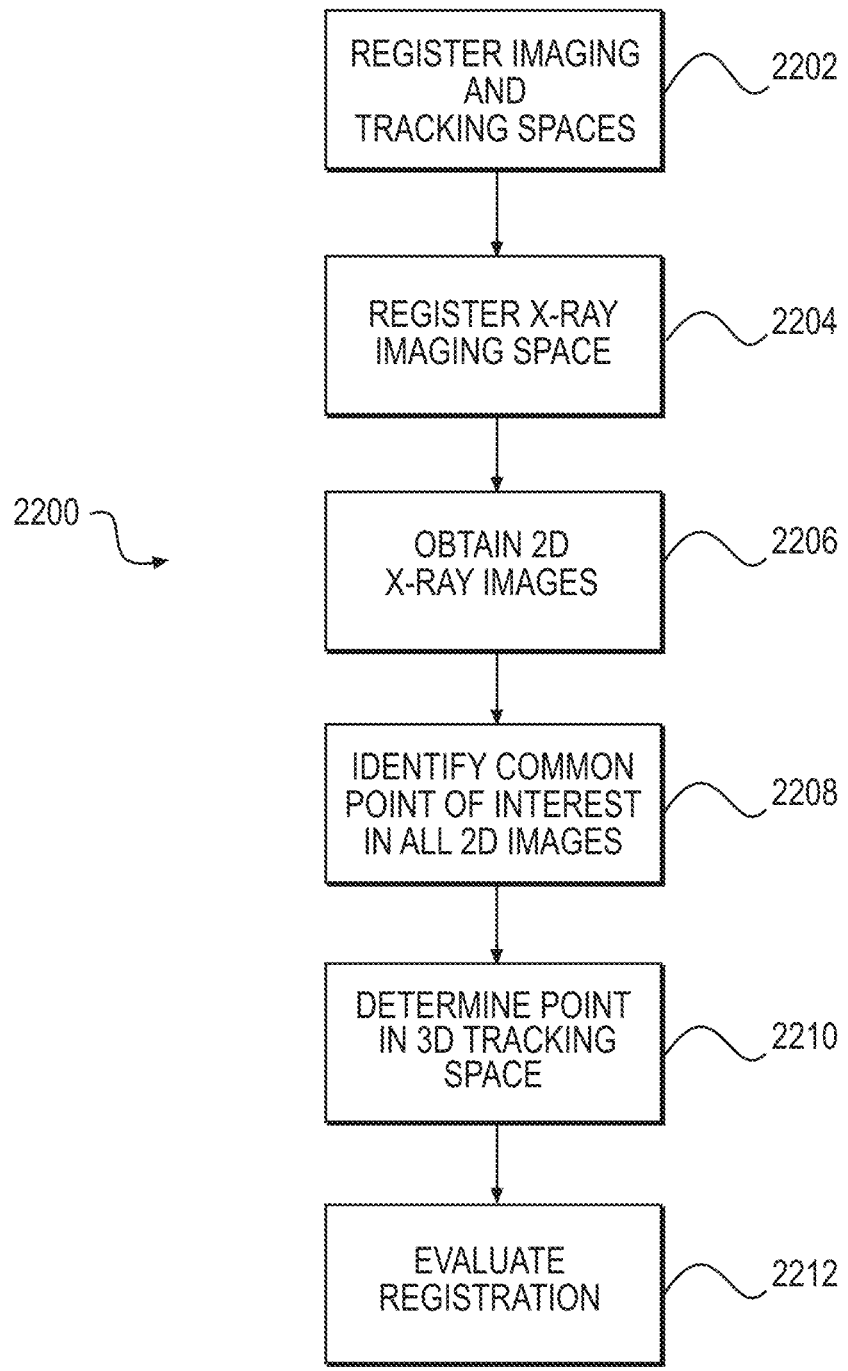
FIG. 22 illustrates a third method of checking registration for a surgical system according to some example embodiments.

FIG. 22 illustrates a third method of checking registration for a surgical system according to some example embodiments. In third method 2200 of checking registration for a surgical system, the surgical system comprising fiducials and tracking markers, method 2200 may comprise: using the fiducials and the tracking markers to register a three-dimensional (3D) imaging space of the surgical system with a 3D tracking space of the surgical system (2202); using a tracking fixture of an X-ray imaging system to register an X-ray imaging space of the X-ray imaging system to the 3D tracking space (2204); obtaining a plurality of two-dimensional (2D) X-ray images corresponding to the 3D tracking space (2206); identifying a common point of interest in all 2D images (2208); determining a point in the 3D tracking space (2210); and/or evaluating the registration of the 3D imaging space with the 3D tracking space based on locations, orientations, or the locations and the orientations of the vectors in the 3D tracking space (2212).

Figure 23:
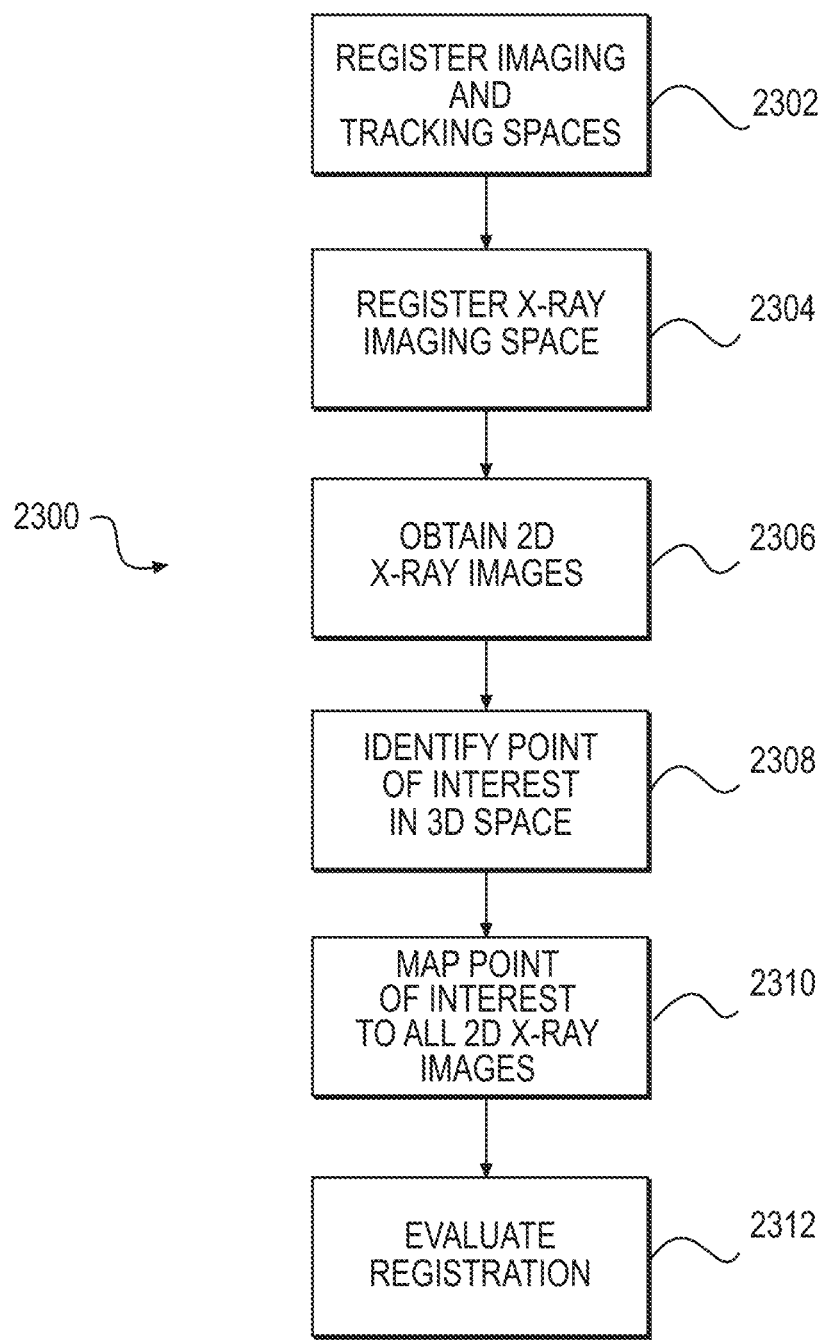
FIG. 23 illustrates a fourth method of checking registration for a surgical system according to some example embodiments.

FIG. 23 illustrates a fourth method of checking registration for a surgical system according to some example embodiments. In fourth method 2300 of checking registration for a surgical system, the surgical system comprising fiducials and tracking markers, method 2300 may comprise: using the fiducials and the tracking markers to register a three-dimensional (3D) imaging space of the surgical system with a 3D tracking space of the surgical system (2302); using a tracking fixture of an X-ray imaging system to register an X-ray imaging space of the X-ray imaging system to the 3D tracking space (2304); obtaining a plurality of two-dimensional (2D) X-ray images corresponding to the 3D tracking space (2306); identifying a point of interest in the 3D imaging space or the 3D tracking space (2308); mapping point of interest to all 2D X-ray images (2310); and/or evaluating the registration of the 3D imaging space with the 3D tracking space based on a location of the point of interest in the 2D X-ray images (2312).

Assuming a registration error between the 3D imaging space and the 3D tracking space, a user may attempt to repair the registration. A first approach could be to conduct a new registration using, for example, an intra-operative CT scan. As such, a new CT would need to be obtained with the registration fixture in place.

A second approach could use the X-ray images taken for the registration check for a new registration. A user could use the x-ray image or images that were taken as a registration check for use in a CT-fluoro registration. Such registration has been described with respect to U.S. patent application Ser. No. 15/289,537, filed on Oct. 16, 2016, which is incorporated herein by reference in its entirety. For example, two x-rays such as an anteroposterior x-ray and a lateral x-ray are obtained while tracking the position of a fluoro registration fixture. The obtained x-rays may be compared to digitally reconstructed radiographs (DRRs) generated through summing the projections of x-rays from a single source through the CT volume. DRRs from different perspectives may be generated iteratively, with orientation parameters modified systematically to minimize a cost function that is based on pixel intensities and the spatial constraints of the two x-ray shots. Once the DRRs match the actual x-ray images, the position of the anatomy relative to fluoro registration fixture at the instant of the two x-rays is known and registration may be achieved. If two or more x-ray images were already taken for the accuracy check, the same x-rays could be used in this registration algorithm to repair the registration. If one x-ray was taken and it was found that registration is off, one more x-ray could be taken and the algorithm could be run.

At least a first advantage of the disclosed methods is that the methods do not require surgical exposure of bone surfaces to perform an accuracy check of the registration of the 3D imaging space with the 3D tracking space. This may be especially useful in minimally invasive, percutaneous, or endoscopic surgery, in which a surgeon may prefer to expose as little of the body interior as possible. At least a second advantage of the disclosed methods is that the point of interest may be more precisely defined and thoughtfully chosen since the user of the methods is dealing with static images. As such, the planes in which X-rays are taken may be selected to achieve high accuracy and easy assessment of identifying offsets (e.g., improper registrations). At least a third advantage of the disclosed methods is that the same X-rays used for the accuracy check of the registration of the 3D imaging space with the 3D tracking space may be used in repairing the registration, assuming the registration is improper.

The foregoing is illustrative of some example embodiments and is not to be construed as limiting thereof. Although some example embodiments have been described, those skilled in the art will readily appreciate that many modifications are possible in the example embodiments without materially departing from the novel teachings and advantages of the present inventive concepts. Accordingly, all such modifications are intended to be included within the scope of the present inventive concepts as defined in the claims.

It should be understood that the example embodiments described herein should be considered in a descriptive sense only and not for purposes of limitation. Descriptions of features or aspects within each example embodiment should typically be considered as available for other similar features or aspects in other example embodiments.

The invention claimed is:

1. A method of checking the accuracy of registration for a surgical system, the surgical system having fiducials and tracking markers, the method comprising:
   using the fiducials and the tracking markers to register a targeted anatomical structure of a patient in a three-dimensional (3D) imaging space of the surgical system with a 3D navigation tracking space of the surgical system;
   using a tracking fixture of an X-ray imaging system to register the X-ray imaging system and an X-ray imaging space of the X-ray imaging system to the 3D navigation tracking space;
   obtaining a two-dimensional (2D) X-ray image of the patient corresponding to the 3D navigation tracking space;
   identifying a point of interest in the 2D X-ray image;

determining a vector in the 3D navigation tracking space that passes through the point of interest, wherein the vector is determined by the surgical system by interpolating between a set of 3D infinite vectors that correspond to a position of a plurality of radio-opaque points on the tracking fixture between an x-ray source and an image intensifier; and checking the accuracy of the registration of the 3D imaging space with the 3D navigation tracking space based on a location, an orientation, or the location and the orientation of the determined vector in the 3D navigation tracking space.

2. The method of claim 1, wherein the surgical system further comprises a processor, and
wherein the vector in the 3D navigation tracking space that passes through the point of interest is determined by the processor.

3. The method of claim 1, wherein the surgical system further comprises a processor,
wherein the vector in the 3D navigation tracking space that passes through the point of interest is determined by the processor, and
wherein the registration of the 3D imaging space with the 3D navigation tracking space based on the location, the orientation, or the location and the orientation of the vector in the 3D navigation tracking space is evaluated by the processor.

4. The method of claim 1, wherein the surgical system further comprises a processor and a display,
wherein the vector in the 3D navigation tracking space that passes through the point of interest is determined by the processor and is shown on the display, and
wherein the registration of the 3D imaging space with the 3D navigation tracking space based on the location, the orientation, or the location and the orientation of the vector in the 3D navigation tracking space is evaluated by an operator of the surgical system using the display.

5. A method of checking the accuracy of registration for a surgical system, the surgical system having fiducials and tracking markers, the method comprising:
using the fiducials and the tracking markers to register a targeted anatomical structure of a patient in a three-dimensional (3D) imaging space of the surgical system with a 3D navigation tracking space of the surgical system;
using a tracking fixture of an X-ray imaging system to register the X-ray imaging system and an X-ray imaging space of the X-ray imaging system to the 3D navigation tracking space;
obtaining a two-dimensional (2D) X-ray image of the patient corresponding to the 3D navigation tracking space;
identifying a point of interest of the patient;
mapping the point of interest to the 2D X-ray image;
determining a vector in the 3D tracking space that passes through the point of interest wherein, the vector is determined by the surgical system by interpolating between a set of 3D infinite vectors that correspond to a position of a plurality of radio-opaque points on the tracking fixture between an x-ray source and an image intensifier; and checking the accuracy of the registration of the 3D imaging space with the 3D navigation tracking space based on a location of the point of interest in the 2D X-ray image; a location, an orientation, or the location and the orientation of the vector in the 3D navigation tracking space;
or the location of the point of interest in the 2D X-ray image and the location, the orientation, or the location and the orientation of the vector in the 3D navigation tracking space.

6. The method of claim 5, wherein the point of interest of the patient is identified by an operator of the surgical system.

7. The method of claim 5, wherein the surgical system further comprises a processor, and
wherein the point of interest is mapped to the 2D X-ray image by the processor.

8. The method of claim 5, wherein the surgical system further comprises a processor, and
wherein the vector in the 3D navigation tracking space that passes through the point of interest is determined by the processor.

9. The method of claim 5, wherein the surgical system further comprises a processor,
wherein the vector in the 3D navigation tracking space that passes through the point of interest is determined by the processor, and
wherein the registration of the 3D imaging space with the 3D navigation tracking space based on the location, the orientation, or the location and the orientation of the vector in the 3D navigation tracking space is evaluated by the processor.

10. The method of claim 5, wherein the surgical system further comprises a processor and a display,
wherein the point of interest is mapped to the 2D X-ray image by the processor and is shown on the display,
wherein the vector in the 3D navigation tracking space that passes through the point of interest is determined by the processor and is shown on the display, and
wherein the registration of the 3D imaging space with the 3D navigation tracking space based on the location of the point of interest in the 2D X-ray image; the location, the orientation, or the location and the orientation of the vector in the 3D navigation tracking space; or the location of the point of interest in the 2D X-ray image and the location, the orientation, or the location and the orientation of the vector in the 3D navigation tracking space is evaluated by an operator of the surgical system using the display.

* * * * *